`US008906303B2`

(12) United States Patent
Ermantraut et al.

(10) Patent No.: US 8,906,303 B2
(45) Date of Patent: Dec. 9, 2014

(54) ASSAYS

(75) Inventors: Eugen Ermantraut, Jena (DE); Thomas Kaiser, Hohlstedt (DE); Jens Tuchscheerer, Jena (DE); Vico Baier, Jena (DE); Torsten Schulz, Jena (DE); Anke Wöstemeyer, Jena (DE)

(73) Assignee: Clondiag GmbH, Jena (DE)

( * ) Notice: Subject to any disclaimer, the term of this patent is extended or adjusted under 35 U.S.C. 154(b) by 570 days.

(21) Appl. No.: 12/922,383

(22) PCT Filed: Mar. 16, 2009

(86) PCT No.: PCT/EP2009/053106
§ 371 (c)(1),
(2), (4) Date: Feb. 2, 2011

(87) PCT Pub. No.: WO2009/112594
PCT Pub. Date: Sep. 17, 2009

(65) Prior Publication Data
US 2011/0124114 A1 May 26, 2011

Related U.S. Application Data

(60) Provisional application No. 61/036,537, filed on Mar. 14, 2008, provisional application No. 61/111,429, filed on Nov. 5, 2008.

(51) Int. Cl.
*G01N 21/00* (2006.01)
*B01L 3/00* (2006.01)

(52) U.S. Cl.
CPC ..... *B01L 3/50273* (2013.01); *B01L 2400/0481* (2013.01); *B01L 2300/0887* (2013.01); *B01L 2300/123* (2013.01); *B01L 2200/025* (2013.01); *B01L 2300/0816* (2013.01); *B01L 2200/0684* (2013.01)
USPC .............................. 422/63; 436/164; 436/174

(58) Field of Classification Search
None
See application file for complete search history.

(56) References Cited

U.S. PATENT DOCUMENTS

| 4,690,907 A * | 9/1987 | Hibino et al. ................. 436/514 |
| 6,843,263 B2 * | 1/2005 | Kuo et al. ....................... 137/14 |

(Continued)

FOREIGN PATENT DOCUMENTS

| EP | 1 279 436 | 1/2003 |
| EP | 1279436 | 1/2003 |

(Continued)

OTHER PUBLICATIONS
Atencia, J. et al. Capillary insert i microcirculatory system, 2006, Lab on a Chip, vol. 6, pp. 575-577.*

*Primary Examiner* — Robert Xu
(74) *Attorney, Agent, or Firm* — Steptoe & Johnston LLP

(57) ABSTRACT

A method for assaying a sample for each of multiple analytes is described. The method includes contacting an array of spaced-apart test zones with a liquid sample (e.g., whole blood). The test zones disposed within a channel of a microfluidic device. The channel is defined by at least one flexible wall and a second wall which may or may not be flexible. Each test zone comprising a probe compound specific for a respective target analyte. The microfluidic device is compressed to reduce the thickness of the channel, which is the distance between the inner surfaces of the walls within the channel. The presence of each analyte is determined by optically detecting an interaction at each of multiple test zones for which the distance between the inner surfaces at the corresponding location is reduced. The interaction at each test zone is indicative of the presence in the sample of a target analyte. Capillary structures of the devices or used in the methods may comprise a matrix and the devices may comprise control elements and methods for assaying of sample may use corresponding controlling activities.

15 Claims, 24 Drawing Sheets

(56) References Cited

U.S. PATENT DOCUMENTS

| | | |
|---|---|---|
| 2002/0185184 A1 | 12/2002 | O'Connor et al. |
| 2003/0008308 A1 | 1/2003 | Enzelberger et al. |
| 2004/0115838 A1 | 6/2004 | Quake et al. |
| 2004/0248167 A1 | 12/2004 | Quake et al. |

FOREIGN PATENT DOCUMENTS

| | | |
|---|---|---|
| WO | WO 02060582 | 8/2002 |
| WO | WO 03015923 | 2/2003 |
| WO | WO 2004/087281 | 10/2004 |

* cited by examiner

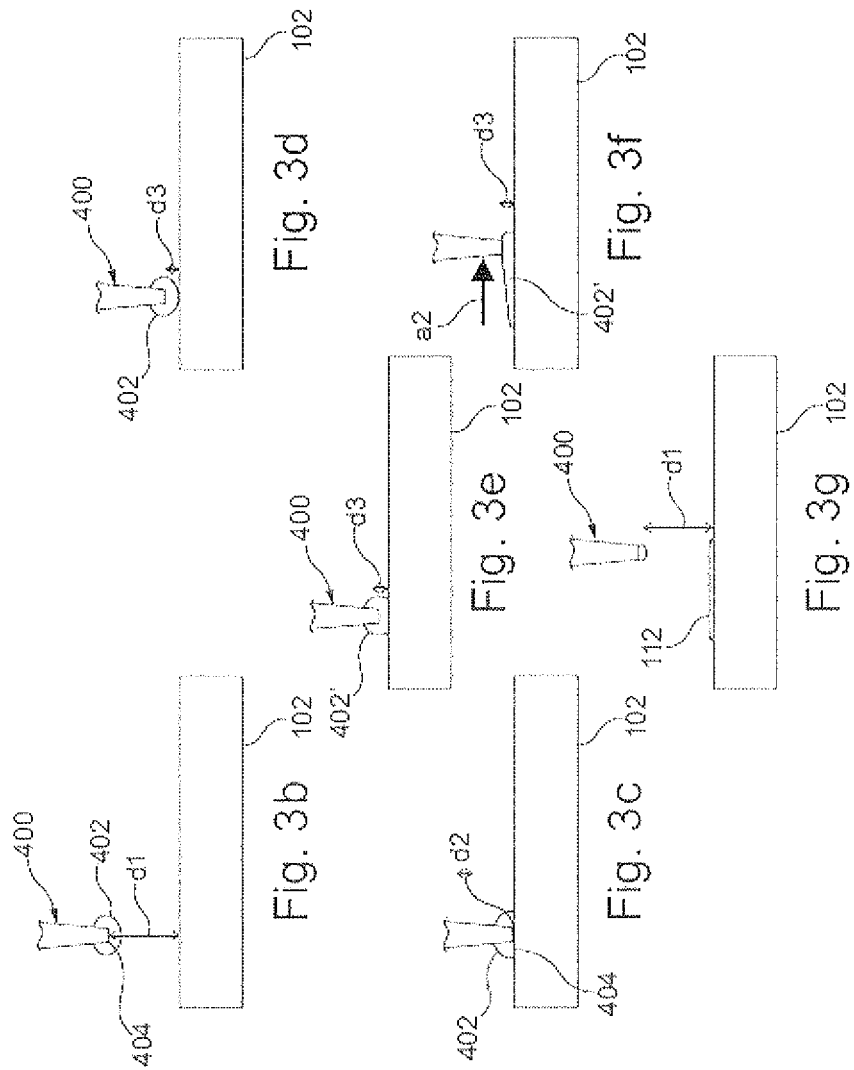

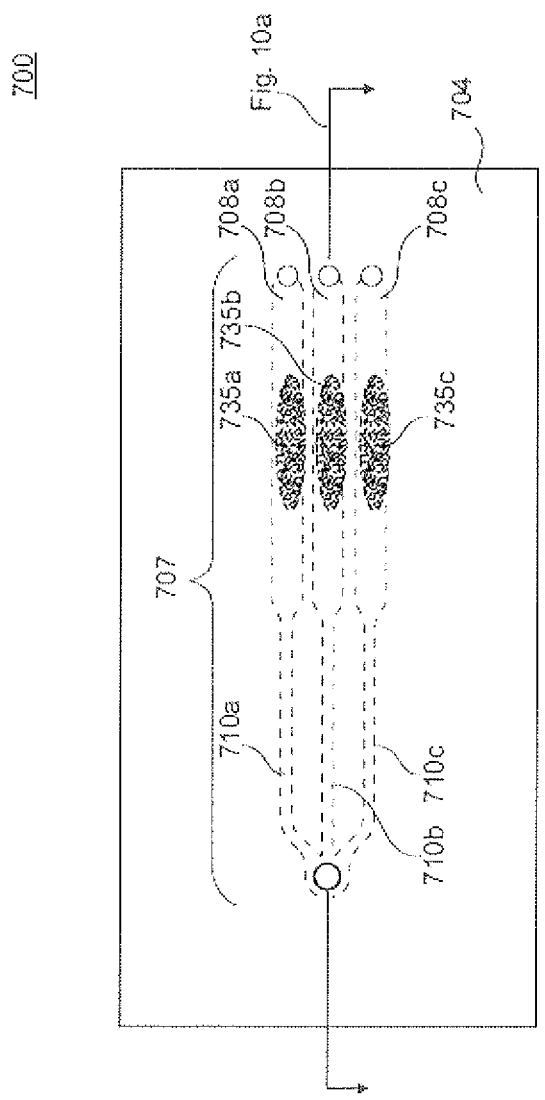

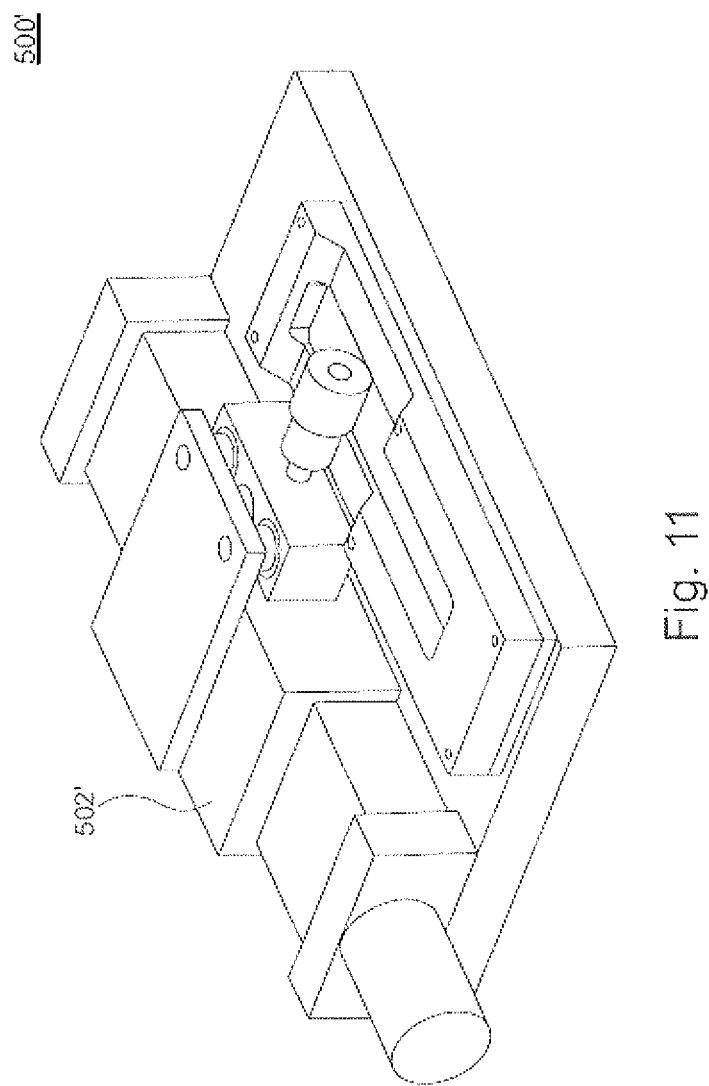

ASSAYS

CLAIM OF PRIORITY

This application claims priority under 35 USC 371 to International Application No. PCT/EP2009/053106, filed on Mar. 16, 2009, which claims priority to U.S. Provisional Application Ser. No. 61/036,537, filed Mar. 14, 2008 and to U.S. Provisional Application Ser. No. 61/111,429, filed Nov. 5, 2008, each of which is incorporated by reference in its entirety.

CROSS REFERENCE TO RELATED APPLICATIONS

This application is related to U.S. provisional application 60/826,678, filed on 22 Sep. 2006; to the U.S. continuation of International Patent Application PCT/EP2005/004923, filed on 6 May 2005, which designates the United States and claims priority to German Patent Application DE 10 2004 022 263, filed on 6 May 2004, the U.S. continuation having Ser. No. 11/593,021 and being filed on 6 Nov. 2006, to International Patent Application PCT/EP2006/068153, filed on 6 Nov. 2006, which designates the United States and claims priority to German Patent Application DE 10 2005 052 752, filed on 4 Nov. 2005, to PCT/EP2006/068155, filed on Nov. 6, 2006 and claims priority to German Patent Application DE 10 2005 052 713, filed on 4 Nov. 2005, to U.S. provisional application 60/867,019 filed on 22 Nov. 2006, to U.S. provisional application 60/915,884, filed on May 3, 2007, to U.S. provisional application 61/036,537, filed on Mar. 14, 2008, to International Patent Application PCT/EP2008/055508, filed on 5 May 2008, which designates the United States and claims priority to U.S. provisional application 60/915,884, filed on May 3, 2007 and U.S. provisional application 61/036, 537, filed on Mar. 14, 2008, and to U.S. provisional application 61/111,429 filed on 5 Nov. 2008.

Each of the foregoing applications is incorporated herein by reference in its entirety.

FIELD OF THE INVENTION

The present invention relates to assays (e.g., assays for one or more analytes in a sample).

BACKGROUND

Assays can be performed to determine the presence of one or more analytes in a sample. Arrays can be used to perform multiple assays (e.g., for each of multiple different analytes) on a sample. Typical arrays include a substrate having multiple spaced apart test zones each having a different probe compound such as a polynucleotide, antibody, or protein. In use, the array is contacted with a sample, which then interacts with the sites of the array. For each site, the interaction can include, for example, binding of a corresponding analyte to probe compounds of the site and/or a chemical reaction between the corresponding analyte and the probe compounds. The reaction results in a detectable product (e.g., a precipitate). The presence and extent of interaction depends upon whether a corresponding analyte is present in the sample.

Typically, the interaction is detected optically (e.g., by fluorescence). For example, optical detection can be performed using an imaging detector (e.g., a CCD) having multiple light sensitive elements (e.g., pixels) spaced apart from one another in at least one (e.g., two) dimensions. Each of the light sensitive elements is positioned to receive light from a different spatial location of the substrate. Thus, light simultaneously detected by multiple light sensitive elements can be combined to form image data in at least one (e.g., two) dimensions of the substrate. The image data can be evaluated to determine the presence and/or extent of interaction at multiple sites of the array.

SUMMARY

The present invention relates to assays (e.g., assays for multiple analytes in a sample).

In one aspect a method comprises:

contacting an array of spaced-apart test zones with a liquid sample, the test zones being disposed between an inner surface of a first substrate and an inner surface of a second substrate of a microfluidic device, at least one of the substrates being flexible, each test zone comprising a probe compound configured to participate in an assay for a target analyte, reducing a distance between the inner surfaces of the first and second substrates at locations of corresponding to the test zones, and sequentially optically determining the presence of an interaction at each of multiple test zones for which the distance between the inner surfaces at the corresponding location is reduced, the interaction at each test zone being indicative of the presence in the sample of a target analyte.

The method can further comprise, for each of multiple test zones, determining the presence of a respective analyte based on the optically determined interaction.

For each of at least some of the test zones, the interaction at each of multiple test zones can be a binding reaction between the analyte and the probe compound of the test zone.

Optically determining can comprise detecting light from each of the test zones using a zero$^{th}$ order detector.

Detecting light from each of the test zones using a zero$^{th}$ order detector can consist essentially of detecting light with the zero$^{th}$ order detector.

The method can further comprise, for each of multiple locations for which the distance between the inner surfaces of the first and second substrates was reduced, subsequently increasing the distance between the inner surfaces after the step of optically determining at the test zone.

Reducing a distance can comprise sequentially reducing the distance between the inner surfaces of the first and second substrates at locations corresponding to the test zones. In this embodiment, the method can further comprise, for each of multiple locations for which the distance between the inner surfaces of the first and second substrates was reduced, subsequently increasing the distance between the inner surfaces after the step of optically detecting binding at the test zone.

Optically determining can comprise sequentially detecting the interaction at each of multiple test zones for which the distance between the inner surfaces at the corresponding location is reduced. In one embodiment, optically detecting comprises simultaneously detecting light from no more than a number N test zones, where $N \le 5$ or $N \le 3$ or $N=1$. Alternatively, optically determining comprises detecting light from each of the test zones using a zero$^{th}$ order detector. Detecting light from each of the test zones using a zero$^{th}$ order detector can consist essentially of detecting light with the zero$^{th}$ order detector.

Optically detecting can comprise translating the microfluidic device with respect to an optical detection zone of an optical detector used to perform the optical determining.

Reducing a distance comprises translating the microfluidic device with respect to a member that applies a compressive force to the microfluidic device. Translating the microfluidic device with respect to the member can comprise rotating at least a portion of the member.

Each test zone can be elongate and define a major axis. Further, translating the microfluidic device can comprise translating the device along a translation axis generally perpendicular to the major axis of each of multiple test zones. E.g., the translation axis and the major axis of multiple of the test zones are perpendicular to within 10° or less or even within 5° or less.

Further, the translation axis and the major axis of most or even of all of the test zones can be generally perpendicular.

The method can further comprise, during the step of translating, reading information contained in a reference code of the microfluidic device, and determining based on the read information a property of each of multiple test zones.

Determining can comprise determining, for each of multiple test zones, a value indicative of when the test zone is in a detection zone of an optical detector used to perform the optical detecting. Further, determining can comprise determining a physiochemical property of test zones of the microfluidic device. E.g., the physiochemical property is indicative of an analyte that can be determined by each of multiple test zones. Further, determining can comprise determining an identity of reagents stored within the microfluidic device prior to use.

A ratio of a length along the major axis to a width along a perpendicular dimension of the test zones can be at least 2.5 or even at least 5.

The step of optically detecting can be performed without first contacting the test zones with a liquid free of the sample after the step of contacting.

Optical determining can comprise exciting and detecting fluorescence from the test zones.

In another aspect, a method comprises:

contacting an array of spaced-apart test zones with a sample, the test zones being disposed between first and second surfaces, each test zone comprising a probe compound configured to participate in an assay for a respective analyte, reducing a distance between the inner surfaces at locations of corresponding to the test zones, and sequentially optically determining the result of the assay at each of multiple test zones for which the distance between the inner surfaces at the corresponding location is reduced.

The method can further comprise, for each of multiple test zones, determining the presence of a respective analyte based on the result of the assay.

For each of at least some of the test zones, the result of the assay can be indicative of a binding reaction between the analyte and the probe compound of the test zone.

Optically determining can comprise detecting light from each of the test zones using a zero$^{th}$ order detector.

Detecting light from each of the test zones using a zero$^{th}$ order detector can consist essentially of detecting light with the zero$^{th}$ order detector.

The method can further comprise, for each of multiple locations for which the distance between the inner surfaces was reduced, subsequently increasing the distance between the inner surfaces after the step of optically determining at the test zone.

Reducing a distance can comprise sequentially reducing the distance between the inner surfaces at locations corresponding to the test zones.

In another aspect, a system comprises:

a microfluidic device reader configured to receive a microfluidic device comprising an array of spaced-apart test zones, the test zones being disposed between an inner surface of a first substrate and an inner surface of a second substrate of the microfluidic device, at least one of the substrates being flexible, each test zone comprising a probe compound configured to participate in an assay for a target analyte, an optical detector configured to detect light from at least one of the test zones when the at least one test zone is in a detection zone of the microfluidic device, a translator configured to translate at least one of the microfluidic device and the detection zone of the optical detector relative to the other, a compressor configured to reduce a distance between the inner surfaces of the first and second substrates at locations corresponding to the detection zone of the optical device, a processor configured to receive a signal from the optical detector, the signal indicative of light detected from a test zone.

The system can be configured to simultaneously optically detect light from no more than a number N test zones, where N≤5, or N≤3, or N=1.

The detector can be a fluorescence detector.

In another aspect, an assay device comprises first and second substrates defining a channel therebetween, at least one of the substrates being flexible, the channel comprising an array of spaced-apart test zones, each test zone comprising a probe compound configured to participate in an assay for a target analyte.

In another aspect, an article of manufacture comprises:

a substrate, and multiple elongate test zones, each test zone comprising a respective probe compound configured to participate in an assay for a target analyte, each test zone defining a major axis and a width perpendicular thereto, and the major axes of the test zones being generally parallel.

In another aspect, a device comprises a cartridge having a microfluidic channel including a capillary inlet having a matrix; and a detection region in fluid communication with the capillary inlet; and a microfluidic flow path having an at least partially deformable wall and in fluid communication with the detection region of the channel.

The device may further comprise a control element.

The microfluidic channel may comprise a first end and a second end, wherein the capillary inlet, the detection region, and at least one opening configured to vent the microfluidic channel may be arranged between the first and the second end.

In another aspect, a device comprises a cartridge having a microfluidic channel including an inlet and a detection region in fluid communication with the inlet, a microfluidic flow path having an at least partially deformable wall and in fluid communication with the detection region of the channel; and a control element.

The inlet or inlet region may be a capillary inlet. The capillary inlet may comprise a matrix.

The microfluidic channel may comprise a first end and a second end, wherein the capillary inlet, the detection region, and at least one opening configured to vent the microfluidic channel may be arranged between the first and the second end.

In another aspect, a device comprises a cartridge including a microfluidic channel comprising a first end and a second end and between the first and the second end an inlet region, a detection region in fluid communication with the inlet region, and at least one opening configured to vent the microfluidic channel; and a microfluidic flow path having an at least partially deformable wall and in fluid communication with the detection region of the channel.

The device may further comprise a control element.

The inlet or inlet region may be a capillary inlet. The capillary inlet may comprise a matrix.

In another aspect, a system comprises a cartridge having a microfluidic channel including a capillary inlet having a matrix and a detection region in fluid communication with the inlet, a microfluidic flow path having an at least partially deformable wall and in fluid communication with the detection region of the channel; and a fluorescence detector including a light source, a condenser lens obtaining a solid angle of 10° or greater, and an objective lens obtaining a solid angle of 10° or greater.

The system may further comprise a control element.

The microfluidic channel may comprise a first end and a second end, wherein the capillary inlet, the detection region, and at least one opening configured to vent the microfluidic channel may be arranged between the first and the second end. In another aspect, a system comprises a cartridge having a microfluidic channel including an inlet and a detection region in fluid communication with the inlet, a microfluidic flow path having an at least partially deformable wall and in fluid communication with the detection region of the channel; a control element; and a fluorescence detector including a light source; a condenser lens obtaining a solid angle of 10° or greater; and an objective lens obtaining a solid angle of 10° or greater.

The inlet may be a capillary inlet. The capillary inlet may comprise a matrix.

The microfluidic channel may comprise a first end and a second end, wherein the capillary inlet, the detection region, and at least one opening configured to vent the microfluidic channel may be arranged between the first and the second end.

In another aspect, a system comprises a cartridge having a microfluidic channel comprising a first end and a second end and between the first and the second end an inlet region, a detection region in fluid communication with the inlet region, and at least one opening configured to vent the microfluidic channel; a microfluidic flow path having an at least partially deformable wall and in fluid communication with the detection region of the channel; and a fluorescence detector including a light source; a condenser lens obtaining a solid angle of 10° or greater; and an objective lens obtaining a solid angle of 10° or greater.

The inlet or inlet region may be a capillary inlet. The capillary inlet may comprise a matrix.

The system may further comprise a control element.

In another aspect, a method comprises introducing a liquid sample into a capillary inlet of a microfluidic channel, wherein the capillary inlet has a matrix, thereby forming a contiguous liquid slug enclosed by the channel and bounded at a first end by a transport fluid; forming a fluid circuit such that the transport fluid provides fluid communication between the first and second ends of the liquid slug; and applying a differential pressure to the first and second ends of the liquid slug via the transport fluid.

The microfluidic channel may comprise and/or may be associated with a control element.

The microfluidic channel may comprise a first end and a second end, wherein the capillary inlet, the detection region, and at least one opening configured to vent the microfluidic channel may be arranged between the first and the second end.

The method may further comprise labeling the analyte with a first fluorescent antibody and a second fluorescent antibody, wherein the first and second fluorescent antibodies have distinct emission wavelengths.

The method may further comprise detecting the analyte including the recording of a first image of the analyte at the emission wavelength of the first fluorescent antibody; recording of a second image of the analyte at the emission wavelength of the second fluorescent antibody; and comparing the first and second images.

In another aspect, a method comprises introducing a liquid sample into a microfluidic channel comprising and/or being associated with a control element thereby forming a contiguous liquid slug enclosed by the channel and bounded at a first end by a transport fluid, forming a fluid circuit such that the transport fluid provides fluid communication between the first and second ends of the liquid slug; and applying a differential pressure to the first and second ends of the liquid slug via the transport fluid.

The microfluidic channel can include an inlet. The inlet may be a capillary inlet. The capillary inlet may comprise a matrix.

The microfluidic channel may comprise a first end and a second end, wherein the capillary inlet, the detection region, and at least one opening configured to vent the microfluidic channel may be arranged between the first and the second end.

The method may further comprise labeling the analyte with a first fluorescent antibody and a second fluorescent antibody, wherein the first and second fluorescent antibodies have distinct emission wavelengths.

The method may further comprise detecting the analyte including the recording of a first image of the analyte at the emission wavelength of the first fluorescent antibody; recording a second image of the analyte at the emission wavelength of the second fluorescent antibody; and comparing the first and second images.

In another aspect, a method comprises introducing a liquid sample into a first end of a microfluidic channel comprising the first end and a second end and between the first and the second end at least one opening configured to vent the microfluidic channel, thereby forming a contiguous liquid slug enclosed by the channel and bounded at a first end by a transport fluid; forming a fluid circuit such that the opening is closed and the transport fluid provides fluid communication between the first and second ends of the liquid slug; and applying a differential pressure to the first and second ends of the liquid slug via the transport fluid.

The microfluidic channel may comprise and/or may be associated with a control element.

The microfluidic channel can further include an inlet or inlet region. The inlet may be a capillary inlet. The capillary inlet may comprise a matrix.

In another aspect, a method comprises introducing a liquid sample into a microfluidic channel including a capillary inlet having a matrix thereby forming a contiguous liquid slug enclosed by the channel and bounded at a first end by a transport fluid, the liquid sample comprising multiple particles, forming a fluid circuit such that the transport fluid provides fluid communication between the first and second ends of the liquid slug, forming a mixture comprising at least a portion of the liquid sample and an optical label by applying a differential pressure to the first and second ends of the liquid slug via the transport fluid, forming multiple complexes, each complex comprising one of the multiple particles and at least one of the optical labels, and detecting complexes present within a subset of the mixture.

The microfluidic channel may comprise and/or may be associated with a control element.

The microfluidic channel may comprise a first end and a second end, wherein the capillary inlet, the detection region, and at least one opening configured to vent the microfluidic channel may be arranged between the first and the second end.

In another aspect a method comprises introducing a liquid sample into a microfluidic channel thereby forming a contiguous liquid slug enclosed by the channel and bounded at a first end by a transport fluid, the liquid sample comprising multiple particles, wherein said microfluidic channel comprises and/or is associated with a control element; forming a fluid circuit such that the transport fluid provides fluid communication between the first and second ends of the liquid slug, forming a mixture comprising at least a portion of the liquid sample and an optical label by applying a differential pressure to the first and second ends of the liquid slug via the transport fluid, forming multiple complexes, each complex comprising one of the multiple particles and at least one of the optical labels, and detecting complexes present within a subset of the mixture.

The microfluidic channel can include an inlet. The inlet may be a capillary inlet. The capillary inlet may comprise a matrix.

The microfluidic channel may comprise a first end and a second end, wherein the capillary inlet, the detection region, and at least one opening configured to vent the microfluidic channel may be arranged between the first and the second end.

In another aspect, a method comprises introducing a liquid sample into a first end of a microfluidic channel comprising the first end and a second end and between the first and the second end at least one opening configured to vent the microfluidic channel, thereby forming a contiguous liquid slug enclosed by the channel and bounded at a first end by a transport fluid; forming a fluid circuit such that the opening is closed and the transport fluid provides fluid communication between the first and second ends of the liquid slug, forming a mixture comprising at least a portion of the liquid sample and an optical label by applying a differential pressure to the first and second ends of the liquid slug via the transport fluid, forming multiple complexes, each complex comprising one of the multiple particles and at least one of the optical labels, and detecting complexes present within a subset of the mixture.

The microfluidic channel may comprise and/or may be associated with a control element.

The microfluidic channel can include an inlet or inlet region. The inlet may be a capillary inlet. The capillary inlet may comprise a matrix.

In another aspect, a method comprises introducing a liquid sample to a bore of a capillary; and introducing at least a portion of the liquid sample into a microfluidic network of a microfluidic device as defined herein above, by reducing a pressure acting on a liquid sample-gas interface of the liquid sample.

The method may further comprise, subsequent to the step of introducing the liquid sample to the bore of the capillary, the connecting of the capillary to the microfluidic device, the liquid sample remaining within the capillary.

Reducing the pressure may be performed by compressing at least a portion of the microfluidic network to displace gas therefrom and subsequently decompressing the at least a portion of the microfluidic network.

The microfluidic network may at least in part be defined by and between first and second generally planar substrates, at least one of the substrates being deformable upon the application of external pressure to compress the at least a portion of the microfluidic network and the at least one substrate tending to resume its previous position upon release of the external pressure to permit decompression of the at least a portion of the microfluidic network.

Further, the microfluidic network may at least in part be defined by a microfluidic channel including an inlet and a detection region in fluid communication with the inlet, and a microfluidic flow path in fluid communication with the detection region, wherein the microfluidic flow path has a wall being at least partially deformable upon the application of external pressure to compress the at least a portion of the microfluidic flow path, and the wall tends to resume its previous position upon release of the external pressure to permit decompression of the at least a portion of the microfluidic flow path.

The method may further comprise combining the liquid sample with one or more reagents present within the microfluidic network to form a mixture. The mixture may comprise at least 90% of the liquid sample that was introduced to the microfluidic network.

The one or more reagents may include a detectable label that reacts with the sample to form a complex including the label and an analyte present in the sample.

The detectable label may also react with analytes immobilized within the microfluidic channel.

The method may further comprise optically detecting a signal indicative of an amount of complex present within a subset of the liquid sample, the subset being present within a detection zone of the microfluidic device.

The method may additionally comprise displacing the subset of liquid sample from the detection zone and introducing a different subset of the liquid sample into the detection zone and optically detecting a signal indicative of an amount of complex present within the different subset.

The method may further comprise performing the step of displacing the subset and introducing the different subset by compressing at least a portion of the microfluidic network, the compressed portion being at least partially offset along the network from the detection zone. The compressing of the portion may comprise compressing a first portion of the microfluidic network and, without first completely releasing the compression, moving a site of the compression along the microfluidic network by an amount sufficient to perform the steps of displacing and introducing.

The method may further comprise performing the step of optically detecting a signal indicative of an amount of complex present within the different subset without first completely releasing the compression of the microfluidic network.

The method may further comprise optically detecting a signal indicative of an amount of optically detectable beads being immobilized within the microfluidic channel.

In another aspect a method comprises introducing a liquid sample to a capillary inlet of a microfluidic network wherein the capillary inlet has a matrix and the microfluidic network is disposed between an inner surface of a first substrate and an inner surface of a second substrate of a microfluidic device, at least one of the substrates being flexible, the liquid sample comprising multiple particles, forming a mixture comprising at least a portion of the liquid sample and an optical label by sequentially reducing a distance between the inner surfaces of the first and second substrates at multiple positions within the microfluidic network, forming multiple complexes, each complex comprising one of the multiple particles and at least one of the optical labels, and detecting complexes present within a subset of the mixture.

The microfluidic network may further comprise and/or be associated with a control element.

In another aspect a method comprises introducing a liquid sample to a microfluidic network, disposed between an inner surface of a first substrate and an inner surface of a second substrate of a microfluidic device, at least one of the substrates being flexible, the liquid sample comprising multiple particles, forming a mixture comprising at least a portion of the liquid sample and an optical label by sequentially reducing a distance between the inner surfaces of the first and second substrates at multiple positions within the microfluidic network, forming multiple complexes, each complex comprising one of the multiple particles and at least one of the optical labels, and detecting complexes present within a subset of the mixture, wherein the microfluidic network comprises or is associated with a control element.

The microfluidic network can include an inlet. The inlet may be a capillary inlet. The capillary inlet may comprise a matrix.

In another aspect a method comprises introducing a total volume V of a liquid sample to a capillary inlet of a microfluidic network wherein the capillary inlet has a matrix and the microfluidic network is disposed between an inner surface of a first substrate and an inner surface of a second substrate of a microfluidic device, at least one of the substrates being flexible, the liquid sample comprising multiple particles, forming a mixture within the microfluidic network, the mixture comprising at least about 90% of the volume V of liquid sample and an optical label, forming multiple complexes, each complex comprising one of the multiple particles and at least one of the optical labels, and detecting complexes present within a subset of the mixture.

The microfluidic network may further comprise and/or be associated with a control element.

In another aspect a method comprises introducing a total volume V of a liquid sample to a microfluidic network disposed between an inner surface of a first substrate and an inner surface of a second substrate of a microfluidic device, at least one of the substrates being flexible, the liquid sample comprising multiple particles, forming a mixture within the microfluidic network, the mixture comprising at least about 90% of the volume V of liquid sample and an optical label, forming multiple complexes, each complex comprising one of the multiple particles and at least one of the optical labels, and detecting complexes present within a subset of the mixture, wherein the microfluidic network comprises or is associated with a control element.

The microfluidic network can include an inlet. The inlet may be a capillary inlet. The capillary inlet may comprise a matrix.

In another aspect, a device is configured to perform a method as defined herein above.

In another aspect a capillary comprises a matrix, wherein said matrix comprises a detectable label that reacts with an analyte or sample to form a complex including the label.

In yet another aspect a method comprises introducing a liquid sample into a microfluidic network via a capillary channel, the capillary channel comprising a matrix, wherein said matrix comprises a detectable label that reacts with an analyte or sample to form a complex including the label.

In another aspect, a method comprises introducing a liquid sample into a microfluidic network, the liquid sample comprising a first set of multiple particles, wherein said microfluidic channel comprises and/or is associated with a control element including a second set of particles; forming a mixture comprising at least a portion of the liquid sample and an optical label; forming multiple complexes, each complex comprising one of the first set of multiple particles and at least one of the optical labels; forming multiple complexes, each complex comprising one of the second set of multiple particles and at least one of the optical labels; and detecting complexes present within a subset of the mixture.

The microfluidic network can include an inlet. The inlet may be a capillary inlet. The capillary inlet may comprise a matrix.

In another aspect, a method comprises introducing a liquid sample comprising multiple particles to a capillary inlet of a microfluidic network, the capillary inlet comprising a matrix comprising optical labels; at least partially dissolving the matrix in the liquid sample thereby forming a mixture comprising at least a portion of the liquid sample and optical label; forming multiple complexes, each complex comprising one of the multiple particles and at least one of the optical labels; and detecting complexes present within a subset of the mixture.

The microfluidic network may further comprise and/or be associated with a control element.

Next, further exemplary embodiments of the devices and methods (e.g., of the devices, systems, capillaries and methods for detecting an analyte) will be explained.

The device or system can further comprise a cap having a sealing member configured to seal with the capillary inlet and form a fluid circuit including the capillary inlet, the microfluidic channel and the microfluidic flow path.

The cap and cartridge may be configured to close irreversibly after forming the fluid circuit.

Alternatively, the cap may be flexibly attached to the cartridge.

Further, the cap and cartridge may be configured to engage in a first relative position such that the cap may be removed and to engage in a second relative position such that the cap can irreversibly be closed after forming the fluid circuit.

In some embodiments, a device or system as described above may comprise at least one opening configured to vent the microfluidic channel. Such an opening or ventilation opening may be located between a detection region and an inlet region.

The opening may provide a fluid connection of an inner end of the inlet region with ambient gas, e.g. the atmosphere surrounding the microfluidic channel or the device or the system. The inner end of the inlet region is opposite to an outer end of the inlet region which is adapted for receiving the sample. For instance, the ventilation opening may be in fluid communication with ambient fluid or ambient gas surrounding the microfluidic channel and/or the cartridge.

The opening configured to vent the microfluidic channel or ventilation opening may be configured to remove gas from the microfluidic channel, e.g. during filling of the device with the sample.

Further, the ventilation opening may be an opening in a wall surrounding the microfluidic channel. The opening may be, for instance, a hole through a wall of the microfluidic channel, Such a hole may provide fluid communication of the inner end of the inlet region with the ambient air.

Further, the ventilation opening may be closable. In some embodiments, the opening will be closed after the capillary inlet is filled with the sample.

The inlet region or inlet or capillary inlet may be movable within the microfluidic channel, e.g. with respect to the opening. For instance, the inlet region may be movable along a longitudinal axis of the microfluidic channel. In one embodiment, the inlet region adapted for receiving the sample may be arranged in such a manner that a movement of the inlet region within the microfluidic channel will allow closing the ventilation opening.

In some embodiments, the opening, in a first relative position of the inlet region within the microfluidic channel, is in fluid communication with the inlet region, and, in a second relative position of the inlet region within the microfluidic channel, is closed. For instance, the device may further comprise a cap having a sealing member configured to seal with the inlet region, wherein the cap is arranged such that closing of the cap moves the inlet region from the first relative position within the microfluidic channel to the second relative position within the microfluidic channel to form a closed fluid circuit including the inlet region, the detection region and the microfluidic flow path.

In further embodiments, the ventilation opening may be configured to introduce gas into the microfluidic channel and/or to remove liquid from and/or introduce liquid into the microfluidic channel.

The detection region may be bounded by at least one surface of the cartridge and at least one surface of a lid. The lid may include a transparent film over the detection region. Further, the lid may be adhesively affixed to the cartridge.

A portion of the fluid circuit can be formed by an elastically deformable wall.

Applying a differential pressure to the first and second ends of the liquid slug can include compressing the elastically deformable wall.

In some embodiments, the microfluidic channel includes a capillary inlet having a matrix. The matrix may include reagents necessary for processing the sample. E.g., the matrix may be a three-dimensional reagent medium.

E.g., the matrix can include reagents selected from the group consisting of a detectable label that can react with the analyte to form a complex including the label, a coagulation inhibitor, and a stabilizing agent. E.g., the matrix can include antibodies labelled with a fluorescent dye and having an affinity for antigens to be detected within the sample.

Further, the matrix may be at least partially porous and/or at least partially amorphous and/or at least partially permeable for fluids and/or at least partially particulate. Further or alternatively, the matrix may have a filter cake-like or substance-cake or cake-like structure. The matrix may also be a flow-through medium.

The matrix may be at least partially dissolvable in the sample. E.g., the matrix can include one or more reagents which are at least partially or even completely dissolvable in a liquid sample such as blood. E.g., the detectable label, the coagulation inhibitor and/or the stabilizing agent may be at least partially dissolvable in the sample.

Further or alternatively, the matrix may comprise freeze-dried reagents. In other words, the matrix may be a lyophilisate containing one or more reagents such as those reagents as described herein. E.g., the freeze dried reagents can be at least partially or even completely dissolvable in a liquid sample such as blood. Further, the detectable label, the coagulation inhibitor and/or the stabilizing agent may be freeze-dried.

Further or alternatively, the matrix may extend essentially over the entire cross sectional area of the capillary inlet. E.g., the matrix at least partially contacts an inner surface of the capillary inlet over the entire cross sectional area of the capillary.

Further or alternatively, the matrix may not extend over the whole length of the capillary inlet. The length of the capillary is determined in the axis perpendicular to the cross sectional axis of the capillary.

The sample can be selected as desired based on the analytes to be determined. Exemplary samples include liquid samples such as water, aqueous solutions, organic solutions, inorganic solutions, bodily fluids of humans and other animals, for example, urine, sputum, saliva, cerebrospinal fluid, whole blood (e.g. venous whole blood) and blood-derived materials such as plasma and sera. In one embodiment, the liquid sample can be blood.

The analytes to be determined can be selected as desired. For example, the analytes can relate to medicine (e.g., diagnostics), research (e.g., drug discovery), industry (e.g. water or food quality monitoring), or forensics. Exemplary analytes to be determined include markers (e.g., diagnostic markers or predictive markers) of physiological conditions such as disease. Such markers include cardiac markers (e.g., natriuretic peptides and members of the troponin family), cancer markers (e.g., nuclear matrix proteins), genetic markers (e.g., polynucleotides), sepsis markers, neurological markers, and markers indicative of pathogenic conditions. The analytes can be indicative of the presence of pathogens (e.g., bacteria, viruses, or fungi).

In a typical embodiment, one or more of the analytes comprise particles such as viruses, bacteria, cells, fungi, or spores. For example, any of the particles described in International Patent Application PCT/EP2006/068153 (which is incorporated herein by reference in its entirety) can be detected. Examples of naturally occurring particles include inter alia prokaryotic cells (e.g. bacterial cells such as *Escherichia coli* or *Bacillus subtilis*), eukaryotic cells (e.g. yeast cells such as *Saccharomyces cerevisiae*, insect cells such as Sf9 or High 5 cells, immortalized cell lines such as HeLa or Cos cells, and primary cells such as mammalian blood cells) or viruses (e.g. phage particles such as M13 or T7 phage). In one embodiment, the particles can be cells such as T-helper cells, e.g. CD3+ cells and/or CD4+ cells.

The labels or probe compounds or capture molecules or moieties can be selected as desired based on the analytes to be determined. Suitable labels or probe compounds for determining the presence of an analyte are described in U.S. provisional application 60/826,678 filed 22 Sep. 2006, which is incorporated by reference in its entirety. A label or a capture molecule or a probe or a probe molecule or a molecular probe is understood to denote a molecule or a complex, which is used for the detection of other molecules due to a particular characteristic binding behavior or a particular reactivity. Exemplary probe compounds include biopolymers such as peptides, proteins, antigens, antibodies, carbohydrates, nucleic acids, and/or analogs thereof and/or mixed polymers of the above-mentioned biopolymers.

Detectable markers or labels or moieties that can be used include any compound, which directly or indirectly generates a detectable compound or signal in a chemical, physical or enzymatic reaction. Preferably, the labels can be selected inter alia from enzyme labels, optical labels, coloured labels, fluorescent labels, chromogenic labels, luminescent labels, radioactive labels, haptens, biotin, metal complexes, metals, and colloidal gold, with fluorescent labels being particularly preferred. All these types of labels are well established in the art. An example of a physical reaction that is mediated by such labels is the emission of fluorescence. Hence, the optical labels can be fluorescent labels.

The methods can further comprise labeling the analyte with a first optical label and a second optical label antibody, wherein the first and second optical label are different. The first and second optical labels can be first and second fluorescent labels which have distinct emission wavelengths. The label can be an antibody. E.g., the method can further comprise labeling the analyte with a first optical label fluorescent antibody and a second fluorescent antibody, wherein the first and second fluorescent antibodies have distinct emission wavelengths.

For instance, for detecting the number of T-helper cells in a liquid sample the matrix can include an anti-CD4+-antibody labelled with a first fluorescent dye (such as phycoerythrine) and an anti-CD3+-antibody labelled with a second fluorescent dye such as (phycoerythrine-Cy5), salts and stabilizing reagents etc.

Detecting the analyte can include recording a first image of the analyte at the emission wavelength of the first fluorescent antibody; recording a second image of the analyte at the emission wavelength of the second fluorescent antibody; and comparing the first and second images.

In some embodiments, the systems may include a fluorescence detector, e.g. a camera. Further, or alternatively the fluorescence detector may include one or more selectable emission filters.

In some embodiments, one or more control elements are used in the detection of an analyte in a sample. E.g., a control element which may be an element of the devices or systems described herein can be at least one element selected from the group consisting of (i) an analyte being immobilized within the microfluidic channel, (ii) an optically detectable bead being immobilized within the microfluidic channel, (iii) a means for determining the volume of the microfluidic channel, (iv) a means for determining a fluorescence background in the microfluidic channel and (v) a means for detecting the filling of the microfluidic channel.

E.g., an analyte and/or an optically detectable bead may be immobilized within the detection region.

Analytes being immobilized within the microfluidic channel may act as positive controls of the analytes to be detected. In other words, an analyte being immobilized within the microfluidic channel may correspond to an analyte being expected to be detected in the assay.

The analyte being immobilized within the microfluidic channel can be a particle, e.g., a cell. Exemplary cells are T-helper cells such as CD3+ and/or CD4+.

In some embodiments, the methods may further comprise the forming of complexes comprising one of the analytes being immobilized within the microfluidic channel and at least one of the optical labels.

The optically detectable beads being immobilized within the microfluidic channel may be optically detectable without being labeled with a detectable label or moiety. E.g., the optically detectable beads being immobilized within the microfluidic channel may be fluorescent beads.

The methods can further comprise detecting complexes present within each of multiple different subsets of the mixture. E.g., within each mixture of the microfluidic device, particles, if present, can combine with detectable label to form complexes. After a suitable incubation period to permit complex formation, the presence of complexes is detected. Examples for detection of complexes are described in International Patent Application PCT/EP2006/068153, which is incorporated by reference in its entirety.

A total volume of the multiple different subsets can be at least 90% of a volume of the liquid sample introduced to the microfluidic device.

The methods can further comprise introducing a total volume V of liquid sample to the microfluidic device wherein a total volume of the mixture can be at least about 90% or at least about 95% of the volume V.

The methods can further comprise detecting complexes present within at least 10% of the total volume of the mixture, e.g. within 10% to 90%, 15% to 50% or 20% to 30% of the total volume of the mixture.

The microfluidic channel can include an inlet and a detection region in fluid communication with the inlet. Further, the microfluidic channel can be a microfluidic channel of a microfluidic device.

The methods can further comprise, prior to introducing a liquid sample into a microfluidic channel, introducing a liquid sample to a bore of a capillary or a capillary inlet.

The capillary is typically a standard capillary (e.g., an end-to-end capillary such as a plastic capillary). An end-to-end capillary includes an internal bore and first and second openings, one at either end of the bore. The capillary bore can comprise a coagulation inhibitor such as heparin. E.g., the capillary can be anti-coagulant coated such as with heparin. In general, the capillary bore is configured to contain a total volume V of liquid sample. Volume V is typically about 25 µl or less (e.g., about 20 µl or less, about 15 µl or less, about 10 µl or less, about 5 µl or less). In general, volume V is about 1 µl or more (e.g., about 3 or 5 or 7.5 µl or more). In some embodiments, the capillary may be an end to end capillary comprising first and second open ends comprising a total volume V, and the step of introducing at least a portion of the liquid sample may comprise introducing at least 90% of the liquid sample into the microfluidic channel.

The methods can further comprise, intermediate the steps of introducing the liquid sample to the capillary inlet and introducing the liquid sample into the microfluidic channel, connecting the capillary to the microfluidic device, the liquid sample remaining within the capillary.

The methods can further comprise optically detecting a signal indicative of an amount of complex present within a subset of the liquid sample, the subset being present within a detection zone or detection region of the microfluidic device.

An exemplary assay for detecting particles such as cells in a liquid sample is described in, for example, in WO 2007/051861, which is incorporated by reference in its entirety. As described in WO 2007/051861, detection can take place in the microfluidic channel. Thus, the microfluidic channel is at least partially optically transparent. For example, the microfluidic channel can be covered by an at least partially optically transmissible layer.

Introducing the liquid sample can be performed by compressing the elastically deformable wall. Compressing the elastically deformable wall can comprise compressing a first portion of the fluid circuit and, without first completely releasing the compression, moving a site of the compression along the fluid circuit by an amount sufficient to perform the steps of displacing and introducing.

The methods can further comprise performing the step of optically detecting a signal indicative of an amount of complex present within the different subset with first completely releasing the compression.

The methods can further comprise intermediate the steps of introducing the liquid sample to the bore of the capillary and introducing at least the portion of the liquid sample into the microfluidic channel, stopping the liquid sample from exiting the capillary.

In some embodiments, a detection region of the microfluidic channel does not support capillary flow of the liquid sample.

Further, at least a part of an interior surface of the microfluidic channel can be hydrophobic.

The methods can further comprise moving at least one of the microfluidic device and an optical detector with respect to one another and subsequently detecting an optical signal indicative of an amount of complex present within a different subset of the liquid sample.

BRIEF DESCRIPTION OF THE DRAWINGS

FIGS. 3b to 3g illustrate a method for forming the test zone of FIG. 3a.

FIG. 5 is only a partial side view.

FIG. 9 illustrates a microfluidic device.

FIG. 11 illustrates an operating system for operating the microfluidic device of any of FIGS. 1, 7, and 9. The operating system can include any or all of the features of the operating system of FIGS. 4 and 5.

FIG. 22 shows the ventilation opening in an open state and FIG. 23 in a closed state. FIG. 24 is a top view on a first end of a capillary inlet.

DETAILED DESCRIPTION

Figure 1:
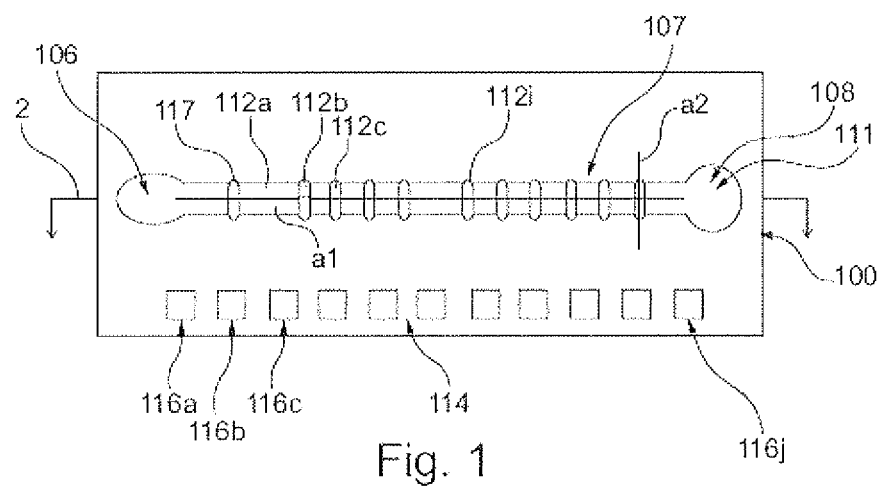
FIG. 1 illustrates a microfluidic device.

A method for assaying a sample to determine the presence (e.g., qualitatively and/or quantitatively) of multiple analytes includes introducing the sample into a channel of a microfluidic device. The microfluidic device can have a single channel or multiple channels, depending on the design and complexity of the assay. In some embodiments, the channel can be defined between opposed inner surfaces of first and second substrates of the device.

In general, a device for performing assays can include a microfluidic flow path that is bounded by at least one deformable surface. For example, where the microfluidic flow path is defined be between opposed inner surfaces of first and second substrates of the device the second substrate can be relatively flexible compared to the first substrate. In another example, a portion of the microfluidic flow path can include a compressible zone. The compressible zone can be a length of the fluid circuit along which at least one wall of the circuit is compressible or deformable. When a localized compressive force is applied to the deformable surface, the surface deforms. Under a sufficient force, the deformable surface can be compressed to a degree that interrupts the microfluidic flow path. Moving the location of the surface deformation relative to the microfluidic flow path can move liquid within the microfluidic flow path, particularly when the deformable surface is compressed to a degree that interrupts the microfluidic flow path.

In some embodiments, the second substrate can be relatively flexible compared to the first substrate. Multiple test zones can be spaced apart along the channel. Each test zone includes an immobilized probe compound configured to participate in an assay for a respective analyte. Typically, each assay includes interaction of a probe compound with the respective analyte or with a respective complex including the analyte and a reagent (e.g., an optical label).

To determine the assay result for each test zone, the outer surface of the second substrate can be subjected to a localized compressive force. The compressive force causes a localized reduction of the distance separating the inner surfaces of the first and second substrates. The location of the localized distance reduction overlaps an optical detection zone defined within the channel. As the distance is reduced, mobile material (e.g., sample, unbound optical probes, and/or reagents) is displaced from between the substrates at the detection zone. The microfluidic device is translated so that the test zones pass sequentially through the detection zone. For each test zone, the assay result is optically determined (e.g., by fluorescence) as the test zone passes through the detection zone. The presence of each analyte is determined (e.g., quantitatively and/or qualitatively) based on the assay result.

The assay results can typically determined without first contacting the test zones with a wash solution after contacting the test zones with the sample.

The analytes to be determined can be selected as desired. For example, the analytes can relate to medicine (e.g., diagnostics), research (e.g., drug discovery), industry (e.g. water or food quality monitoring), or forensics. Exemplary analytes to be determined include markers (e.g., diagnostic markers or predictive markers) of physiological conditions such as disease. Such markers include cardiac markers (e.g., natriuretic peptides and members of the troponin family), cancer markers (e.g., nuclear matrix proteins), genetic markers (e.g., polynucleotides), sepsis markers, neurological markers, and markers indicative of pathogenic conditions. The analytes can be indicative of the presence of pathogens (e.g., bacteria, viruses, or fungi).

The probe compounds of the test zones can be selected as desired based on the analytes to be determined. Exemplary probe compounds include polynucleotides, antibodies, and proteins.

The sample liquid can be selected as desired based on the analytes to be determined. Exemplary samples include water, aqueous solutions, organic solutions, inorganic solutions, bodily fluids of humans and other animals, for example, urine, sputum, saliva, cerebrospinal fluid, whole blood and blood-derived materials such as plasma and sera.

Figure 2:
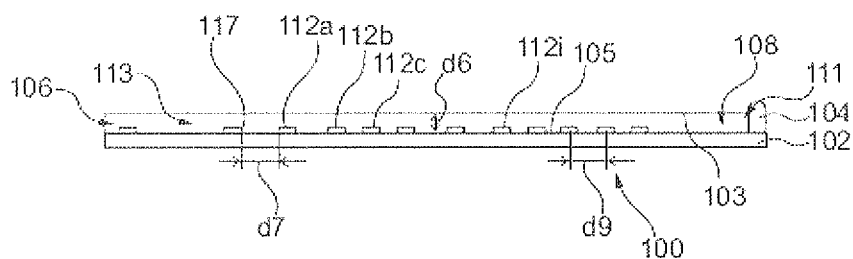
FIG. 2 is a side view of the microfluidic device of FIG. 1.
Figure 4:
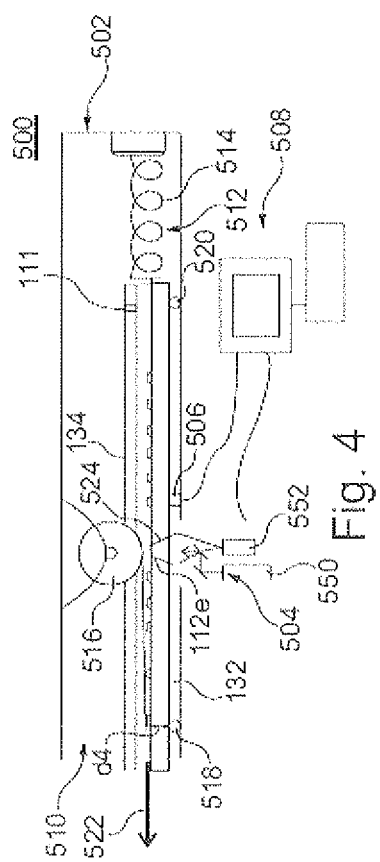
FIGS. 4 and 5 are side views of a system configured to operate the microfluidic device of FIG. 1.

Referring to FIGS. 1, 2, and 4 a microfluidic device 100 and an operating system 500 can be used to assay a sample to determine the presence (e.g., qualitatively and/or quantitatively) of multiple analytes. Microfluidic device 100 includes first and second substrates 102,104 defining a microfluidic network 107 including an inlet 106 and, in communication therewith, a channel 110 and a reservoir 108. Multiple spaced apart test zones 112$i$ are disposed within channel 110. Each test zone 112$i$ includes one or more reagents (e.g., probe compounds) configured to participate in an assay for an analyte. Channel 110 also includes a reference zone 117. Device 100 also includes a reference pattern 114 including multiple indicia 116$j$. Reference pattern 114 provides information related to spatial properties of test zones 112$i$.

Operating system 500 includes a housing 502, a detector 504, a reference pattern reader 506, and a processor in communication with detector 504 and pattern reader 508. Detector 504 is an optical fluorescence detector that detects interaction between a sample and test zones 112$i$. Detector 504 includes a light source 550 (e.g., a light emitting diode or a laser diode) and a zero$^{th}$ order light sensitive detector 552 (e.g., a photomultiplier tube or a photodiode, such as an avalanche photodiode). Reference pattern reader 506 reads reference pattern 114 of device 100 during operation of system 500.

We now discuss microfluidic device 100 and system 500 in greater detail.

First substrate 102 is typically optically transmissive (e.g., clear) with respect to a wavelength of light useful for exciting and detecting fluorescence from fluorescent labels. For example, first substrate 102 may transmit at least about 75% (e.g., at least about 85%, at least about 90%) of incident light in a least one wavelength range between about 350 nm and about 800 nm. First substrate 102 can be formed of, for example, a polymer, glass, or silica. Second substrate 104 is typically formed of a pliable or flexible material (e.g., an elastomeric polymer). First substrate 102 may be less flexible than second substrate 104. For example, first substrate 102 may be substantially rigid (e.g., sufficiently rigid to facilitate handling of device 100).

Channel 110 is a capillary channel. A sample 113 applied to inlet 106 migrates along channel 110 by capillary force. Channel 110 is oriented along a major axis a1. Reservoir 108 includes a vent 111 to prevent gas buildup ahead of the sample.

Each test zone 112$i$ typically includes a reagent (e.g., a probe compound) configured to provide a detectable interaction in the presence of an analyte. The interaction can include, for example, binding of a corresponding analyte to a probe compound of the test site and/or a chemical reaction between the corresponding analyte and the probe compound. The reaction results in a detectable product (e.g., a precipitate). Exemplary probe compounds include proteins, antibodies, and polynucleotides. Suitable probe compounds for determining the presence of an analyte are described in U.S. provisional application 60/826,678 filed 22 Sep. 2006, which is incorporated by reference in its entirety.

Referring also to FIG. 3$a$, each test zone 112$i$ is elongate having a major axis a2 oriented generally perpendicular to major axis a1 of channel 110. Typically, a ratio of a length along major axis a2 to a width w along a perpendicular dimension of the test zones 112 is at least 2.5 (e.g., at least 5). The length along axis a2 is typically at least about 200 μm (e.g., at least about 350 microns) and typically about 2000 μm or less (e.g., about 1000 μm or less, about 750 μm or less). Width w is typically at least about 25 μm (e.g., at least about 50 microns) and typically about 500 μm or less (e.g., about 250 μm or less, about 150 μm or less). In an exemplary embodiment, test zones 112 are about 500 μm long and about 100 μm wide.

As seen in FIG. 2, test zones 112$i$ are spaced apart from adjacent test zones by a distance d7 along channel 110. Distance d7 between test zones 112$i$ is discussed further below in relation to a detection zone of detector 504.

Test zones 112$i$ can be formed as desired. In general, the reagents are contacted with the first substrate. Then, the reagents and substrate are relatively translated laterally to form an elongated test zone.

Referring to FIGS. 3$b$-3$g$, a method for forming test zones 112$i$ includes dispensing reagents from a capillary spotter 400 onto first substrate 102. In FIG. 3$b$, an amount (e.g., between about 2 and 8 nl, between about 3 and 5 nl) of reagent solution 402 containing one or more probe compounds is introduced to a distal tip 404 of a capillary of a capillary spotter. Distal tip 404 typically has a diameter of between about 80 and 120 μm (e.g., about 100 μm). Reagent solution 402 and substrate 102 are initially separated (e.g., not in contact) by a distance d1. Typically, d1 is at least about 250 μm (e.g., about 500 μm).

In FIG. 3$c$, tip 404 and substrate 102 are brought to a smaller separation d2 so that reagent solution 402 contacts a location of substrate 102. At the smaller separation d2, distal tip 404 is adjacent the location of substrate 102 (e.g., touching so that d2 is zero). Distal tip 404 and substrate 102 are maintained for a time (e.g., about 1 second or less, about 0.5 seconds or less, about 0.25 second or less) at separation d2 in the adjacent (e.g., touching) position. In some embodiments, the time for which distal tip 402 is maintained in the adjacent (e.g., touching) position is indistinguishable from zero.

In FIG. 3$d$, distal tip 404 and substrate 102 are moved to an intermediate separation d3 in which distal tip 404 and substrate remain connected by reagent solution 402 of distal tip 404. Typically, intermediate separation d3 is at least about 5 μm (e.g., at least about 10 μm) and about 30 μm or less, about 25 μm or less). In an exemplary embodiment, intermediate separation d3 is about 20 μm.

In FIG. 3$e$, distal tip 404 and substrate 102 are maintained at intermediate separation d3 for an incubation time so that at least some (e.g., at least about 10%, at least about 25%, at least about 40%) of reagent solution 402 at the distal tip evaporates so that only a remaining portion 402' of reagent solution 402 remains. Typically, only about 75% or less (e.g., about 50% or less) of reagent solution 402 evaporates to leave solution 402' remaining. The incubation time depends on the nature of the solution 402 (e.g., the probe compound concentration and the solvent vapor pressure) and distal tip 404 environment (e.g., the relative humidity and temperature). Typical incubation times are longer (e.g., at least 5 times as long, at least 10 times as long, at least 20 times as long, at least about 35 times as long) than the period of time for which the tip and substrate are in the adjacent position d2. Exemplary incubation times are least about 5 seconds (e.g., at least about 10 seconds at least about 20 seconds, at least about 25 seconds).

In FIG. 3f, after the incubation time at intermediate separation d3, at least one of the distal tip 404 and substrate 102 are moved laterally relative to the other to dispense reagent solution 402' along a major axis a2. In FIG. 3g, at the completion of the lateral movement, distal tip 402 and substrate 102 are separated so that they are no longer connected by the reagent solution. For example, distal tip 404 and substrate 102 can be returned to initial separation d1. The method can be repeated (e.g., using different reagent solution) to dispense elongate test zones at each of multiple locations of the substrate.

In general, the vertical separation of the distal tip and substrate is changed by moving the distal tip relative to the substrate. In general, the lateral translation of the distal tip and substrate is performed by translating the substrate relative to the distal tip. Exemplary reagent solutions, probe compounds, and dispensing devices are described in U.S. provisional application 60/826,678 filed 22 Sep. 2006, which is incorporated by reference in its entirety.

Figure 3A:
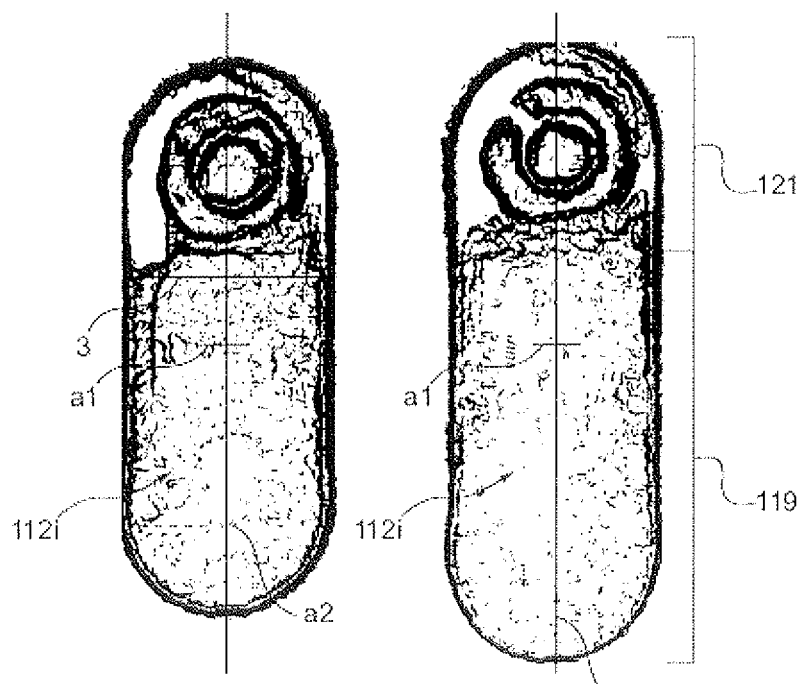
FIG. 3a shows top views of two test zones of the microfluidic device of FIG. 1.
Figure 8A:
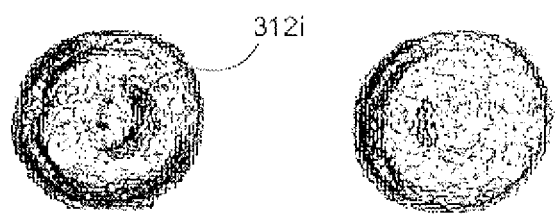
FIGS. 8a and 8b are each top views of two test zones of the microfluidic device of FIG. 7.
Figure 8B:
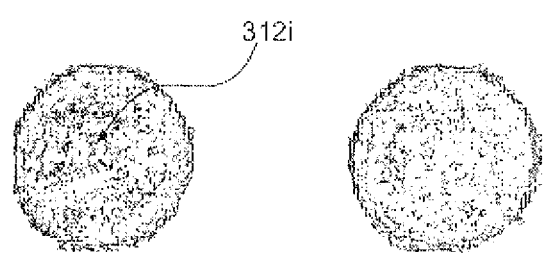

As seen in FIG. 3a and referring also to FIGS. 8a and 8b, the method for producing elongate test zones 112i provides a more homogenous distribution of probe compounds than a dispensing method that omits the step of lateral moving the distal tip and substrate. Test zones 112i include a first portion 119 and a second portion 121. The distribution of probe compounds in the first portion 119 is more homogenous than in second portion 121 or in test zones 312i, which were prepared without the step of lateral movement.

Returning to FIG. 1, reference zone 117 produces a response detectable by detector 504 independent of the presence of any analyte in a sample. Reference zone 117 typically includes a fluorescent medium (e.g., a polymer or immobilized fluorescent molecule). Reference zone 117 is discussed further below in regard to operation of system 500.

Indicia 116j of reference pattern 114 are configured to be read by reference pattern reader 506 of system 500. Indicia 116j are composed of magnetic material (e.g., magnetic ink). Pattern reader 506 can detect the presence of indicia 116j. Reference pattern 114 is discussed further below in regard to operation of system 500.

Returning to FIG. 4, housing 502 of operating system 500 includes an opening 510 to receive device 100, a compression system including a compression roller 516 and support rollers 518,520, and a translation actuator 512 including a damped spring 514. When device 100 is received within housing 500, detector 504 defines an optical detection zone 524 within channel 110. In use, device 100 is translated with respect to detection zone 524. Test zones 112i sequentially pass into and out of the detection zone. Detector 504 sequentially detects the interaction between a sample and successive test zones 112i. Detector 504 also senses reference zone 117.

Figure 6:
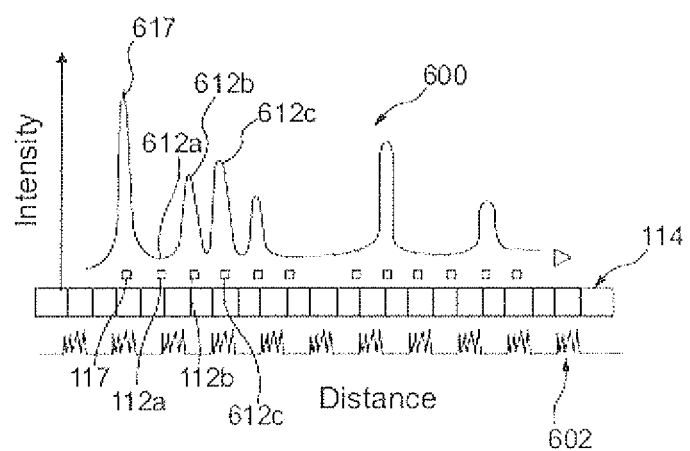
FIG. 6 illustrates fluorescence intensity data as a function of position along a channel of the microfluidic device of FIG. 1.

Referring to FIG. 6, detector 504 outputs a signal 600 as a function of the distance (relative or absolute) that device 100 is translated. Signal 600 includes a peak 617 indicative of reference zone 117 and peaks 612i indicative of the interaction at each zone 112i. Simultaneously, pattern reader 506 outputs a signal 602 indicative of indicia 116i as a function of distance that device 100 is translated. Because indicia 116i are related spatially to test zones 112i, processor 508 can determine when detection zone 524 coincides with a particular test zone even if that test zone exhibits no signal (e.g., as for test zone 112a which exhibits a signal 612a that is indistinguishable from zero). Reference zone 117 and corresponding signal 617 can be used alternatively or in combination with signal 602 to determine which regions of signal 600 correspond to particular test zones.

We next discuss the compression system. In use, the compression system compresses device 100 to reduce the distance between substrates 102,104 within channel 110. When device 100 is received within housing 502, an outer surface 132 of first substrate 102 is oriented toward support rollers 518,520 and an outer surface 134 of second substrate 104 is oriented toward compression roller 516. A distance d4 between support rollers 518,520 and compression roller 516 is less than a thickness t1 (FIG. 5) of device 100. Because second substrate 104 relatively flexible as compared to first substrate 102, compression roller 516 compresses second substrate 104 causing a local reduction in distance d6 between inner surface 103 of second substrate 104 and inner surface 105 of first substrate 102.

In the relaxed state (e.g., uncompressed state) (FIG. 2), distance d6 is typically at least about 25 μm (e.g., at least about 50 μm, at least about 75 μm). In the uncompressed state, distance d6 is typically about 500 μm or less (e.g., about 250 μm or less). In the locally reduced distance state (e.g., locally compressed state) (test zone 112e in FIG. 4), distance d6 is typically about 15 μm or less (e.g., about 10 μm or less, about 5 μm or less, e.g., about 2.5 μm or less). Examples of fluorescence detection performed between surfaces separated by a reduced distance state are described in U.S. continuation of International Patent Application PCT/EP2005/004923, which is incorporated by reference in its entirety.

Figure 5:
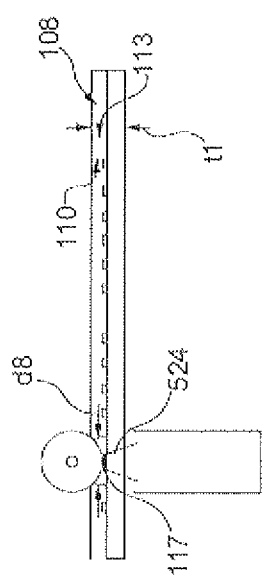

As seen in FIGS. 4 and 5, the compression system reduced distance d8 within channel 110 over only a portion of the length of channel 110. Typically, distance d8 is about 5 times the length or less (e.g., about 3 times the length or less, about 2 times the length or less, about the same as) than distance d7 separating test zones 112i.

Typically, distance d7 is large enough that optical detection zone 524 defined by detector 504 encompasses fewer than all (e.g., 5 or fewer, 3 or fewer, 2 or fewer) of test zones 112i within channel 110. In an exemplary embodiment, d7 is large enough that a width of detection zone 524 along major axis a1 of channel 110 does not simultaneously contact more than 3 (e.g., not more than two, not more than one) test zone 112i. A width of detection zone 524 perpendicular to major axis a1 of channel 110 is typically about the same as or less (e.g., no more than 75% of, no more than 50% percent of, no more than 30% of) the length of test zones 112i along axis a2 thereof.

In use, sample liquid is applied to inlet 106. Capillary force draws the sample along channel 110 toward reservoir 108. The sample liquid contacts test zones 112i along channel 110. Analytes within the sample interact with probe compounds of the test zones. After a suitable incubation time, device 100 is inserted into housing 500 to compress spring 514 of translation actuator 512. During insertion of device 100, compression roller 516 and support rollers 520 are spaced apart so that device 100 is not compressed. Once device 100 is fully inserted, detection zone 524 is positioned approximately overlapping reference zone 117. Compression roller 516 locally compresses channel 110 (FIG. 5).

When the interactions between the analytes of the sample and the test zones 112i are ready to be determined (e.g., after an incubation period), translation actuator 512 translates device 100 with respect to detection zone 524 of detector 504 (FIG. 4). Test zones 112i pass sequentially through detection zone 524 and are illuminated with light from light source. Compression roller 516 is arranged so that the localized reduction of distance d6 corresponds spatially to detection zone 524. Accordingly, light detector sequentially detects light from test zones 112$i$ while each is in the locally reduced distance state (e.g., locally compressed state) (test zone 112$e$ in FIG. 4). Fluorescence arising from each test zone is collected by lens and detected by light detector. The sequential localized reduction of distance d6 and optical determination continues until each test zone has translated through detection zone 524.

In addition to the probe compounds of each test zone and analytes, other materials are present in channel 110 between inner surface 103 of second substrate 104 and inner surface 105 of first substrate 102. Examples of such materials include sample concomitants and reagents (e.g., unbound or un-reacted optical probes). These materials typically produce background emission (e.g., fluorescence or scattered light) that is not associated with the interaction of the sample with test zones 112$i$. The intensity of the background emission is generally proportional to the amount of such materials remaining between the inner surfaces at the location corresponding to detection zone 524. The intensity of the optical signal that is indicative of the interaction at each test zone, however, is spatially localized in the vicinity of that test zone. Light detector receives and detects both fluorescence indicative of the interaction and the background emission.

Referring to FIGS. 9, 10$a$, and 11, a microfluidic device 700 and an operating system 500' can be used to assay a sample to determine the presence (e.g., qualitatively and/or quantitatively) of one or more analytes. In a typical embodiment, one or more of the analytes comprise particles such as viruses, bacteria, cells, fungi, or spores. For example, any of the particles described in International Patent Application PCT/EP2006/068153 (which is incorporated by reference in its entirety) can be detected.

Microfluidic device 700 includes first and second substrates 702, 704 defining a microfluidic network 707 including an inlet 706 and, in communication therewith, multiple channels 710$a$,710$b$,710$c$ each having a respective reservoir 708$a$,708$b$,708$c$. Each reservoir includes a reagent material 709$a$,709$b$,709$c$ (e.g., a probe compound) configured to participate in an assay for an analyte. Device 700 may include a reference pattern 114 including multiple indicia 116$j$ (not shown in FIGS. 9, 10$a$, 11) which may be the same as that discussed above.

Operating system 500' includes a housing 502', a detector 504', a reference pattern reader (not shown), and a processor in communication with detector 504' and pattern reader. Detector 504 is an optical fluorescence detector that detects complexes comprising an analyte (e.g., a particle) and a detectable label (e.g., an optical label). Examples of suitable labels are described in International Patent Application PCT/EP2006/068153, which is incorporated by reference in its entirety. Detector 504' includes a light source 550' (e.g., a light emitting diode or a laser diode) and an optical detector 552' (e.g., a first order detector such as a diode array or a multidimensional detector (e.g., an imaging detector such as a charge coupled detector)). The optical detector typically and spatially selectively detects light from a respective detection zone defined within each channel of the microfluidic device.

We now discuss microfluidic device 700 and system 500' in greater detail.

First substrate 702 is typically optically transmissive (e.g., clear) with respect to a wavelength of light useful for exciting and detecting fluorescence from fluorescent labels. For example, first substrate 702 may transmit at least about 75% (e.g., at least about 85%, at least about 90%) of incident light in a least one wavelength range between about 350 nm and about 800 nm. First substrate 702 can be formed of, for example, a polymer, glass, or silica. Second substrate 704 is typically formed of a pliable or flexible material (e.g., an elastomeric polymer). First substrate 702 may be less flexible than second substrate 704. For example, first substrate 702 may be substantially rigid (e.g., sufficiently rigid to facilitate handling of device 700).

Channels 710$a$-710$c$ typically support movement of liquid sample therein but are typically not capillary channels (i.e., liquid typically does not move within the channels of device 700 by capillary action). For example, one or more internal surfaces of the channels may be hydrophobic to inhibit capillary movement of the liquid sample. Alternatively, or in combination, the internal dimensions of the channels may be too large to permit capillary forces to drive substantial movement of the sample therein. Of course, in some embodiments, the channels may be capillary channels.

Device 700 is shown with 3 channels and corresponding reservoir but generally has a number N channels and corresponding reservoirs where N is at least 1 and is typically less than 20.

Each reservoir 708$i$ typically includes a reagent 735$i$ (e.g., a detectable label such as an optical label) configured to provide a detectable interaction in the presence of an analyte. The interaction can include, for example, binding of a corresponding analyte to a label to form complex comprising the analyte and one or more of the labels. Examples of such complexes are described in International Patent Application PCT/EP2006/068153 (which is incorporated by reference in its entirety). Each reagent is typically configured to permit detection of a different analyte.

Referring to FIGS. 10$b$-10$f$, device 700 can be operated as follows. An amount of liquid sample 738 (e.g., a biological liquid such as blood, saliva, or urine) is introduced to a capillary 736. Capillary 737 is typically a standard capillary (e.g., an end-to-end capillary such as a plastic capillary). An end-to-end capillary includes an internal bore and first and second openings, one at either end of the bore. The capillary may be anti-coagulant coated such as with heparin. Examples of suitable capillaries include 20 µl heparin coated capillaries available from Kabe Labortechnik (Nürnbrecht-Elsenroth, Deutschland; http://www.kabe-labortechnik.de/index.php?sprache=de&akt_seite=startseite_produkte.php). In general, the capillary bore is configured to contain a total volume V of liquid sample. Volume V is typically about 25 microliters or less (e.g., about 20 microliters or less, about 15 microliters or less, about 10 microliters or less). In general, volume V is about 5 microliters or more (e.g., about 7.5 microliters or more).

As seen in FIG. 10$b$, inlet 706 of device 700 is configured to accommodate capillary 736. Sample 737 typically remains within capillary 736 and does not enter the microfluidic device until subjected to an introduction force.

As seen in FIG. 10$c$, an introduction force can be applied to sample 737 by reducing a distance between internal surfaces of substrates 702, 704 to reduce a volume within the microfluidic network. For example, FIG. 10$c$ illustrates a roller moving along an a portion of the microfluidic network. Typically, the compression causes the opposed internal surfaces to contact one another. As the volume within the channel increases following decompression of a given region of channel, a reduction in the gas pressure acting upon an internal surface 739 of the liquid sample 737 causes the sample to be forced into the microfluidic network. The compression and decompression can be performed in a single continuous movement of roller 716 along the microfluidic network or can be performed sequentially in multiple steps as in a peristaltic fashion.

Figure 10A:
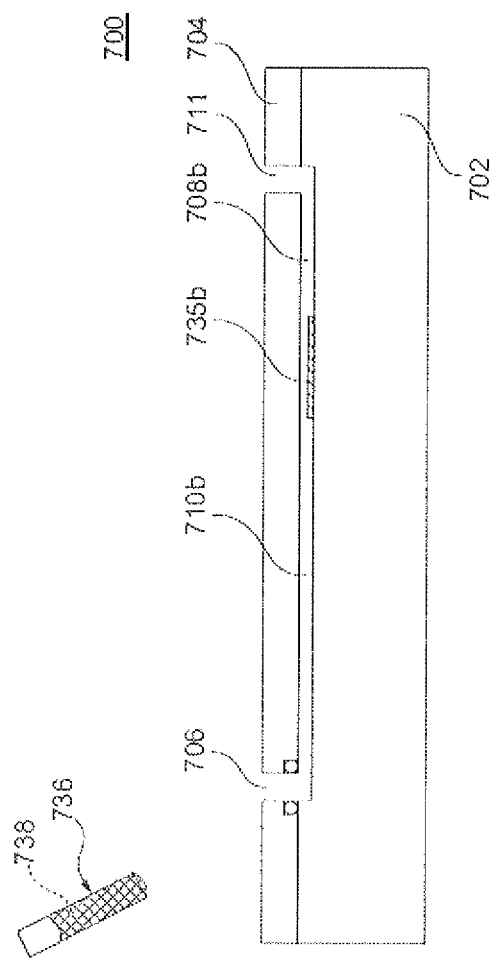
FIG. 10a is a cross-sectional side view of the microfluidic device of FIG. 9 and also illustrates a capillary tube containing liquid sample material.
Figure 10B:
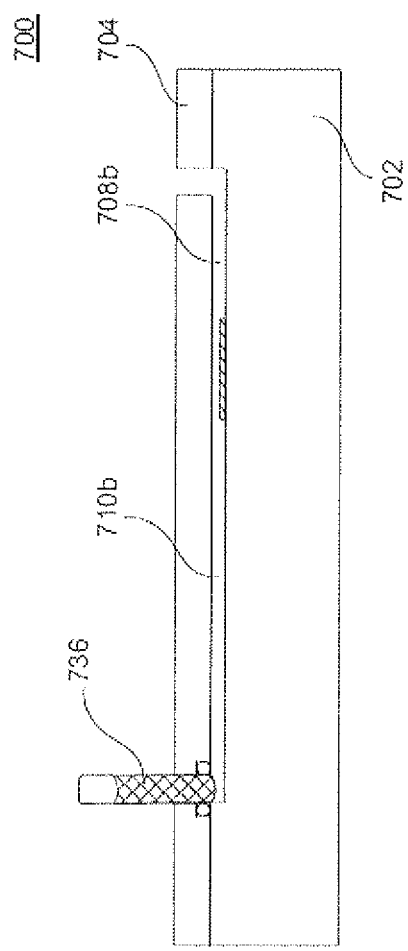
FIG. 10b illustrates the microfluidic device of FIG. 10a with the capillary tube having been connected with an inlet of the microfluidic device, the liquid sample not having entered a microfluidic network of the microfluidic device.
Figure 10C:
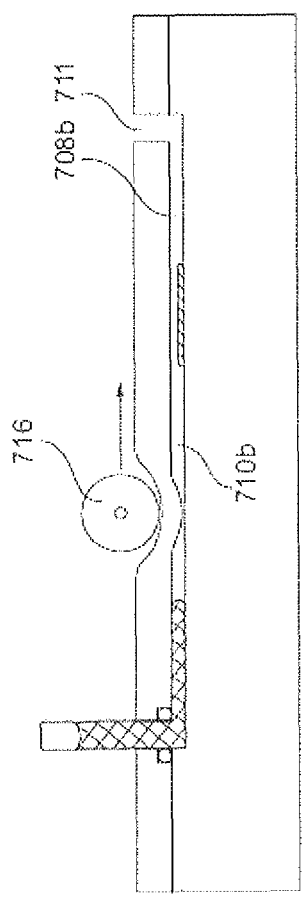
FIG. 10c illustrates the microfluidic device of FIG. 10c with a portion of the liquid sample having been drawn from the sample capillary into the microfluidic network of the microfluidic device.
Figure 10D:
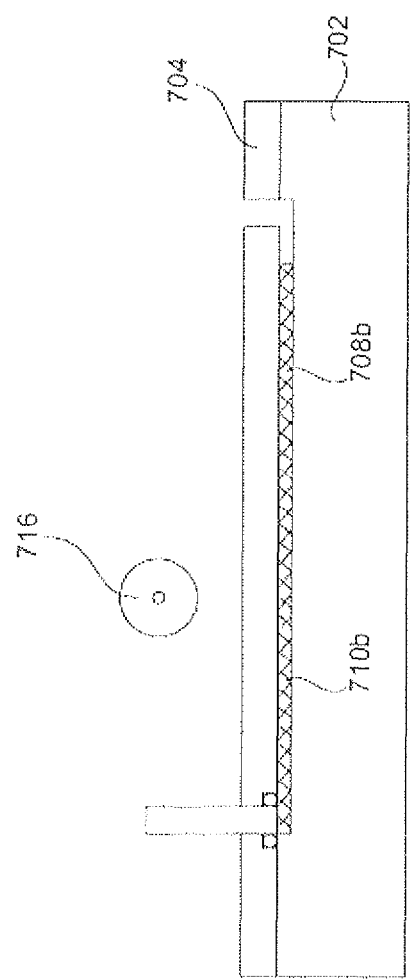
FIG. 10d illustrates the microfluidic device of FIG. 10c with the step of drawing the liquid sample from the sample capillary into the microfluidic network of the microfluidic device having been completed.
Figure 10E:
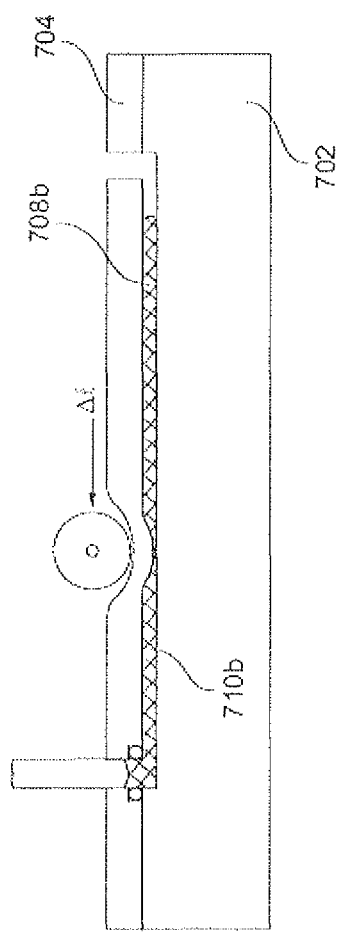
FIG. 10e illustrates the microfluidic device of FIG. 10d with a portion of the liquid sample being moved a distance Δ1 along a length of the microfluidic network.

As seen in FIG. 10d, substantially all (e.g., at least 70%, at least 80%, at least 90%, at least 95%, essentially all) of the volume V of liquid sample 737 is drawn into the microfluidic network. In an exemplary embodiment, at least 90% of volume V is drawn into the network.

Liquid sample within the microfluidic network enters each of channels 710i and reservoirs 708i and mobilizes the reagents within each reservoir to form a mixture. Typically, formation of the mixture is assisted causing bulk motion of the liquid sample within the microfluidic network. Such bulk motion is typically caused by compression and decompression of the microfluidic device to reduce an internal distance between substrates 702,704. The compression and decompression can be performed in a peristaltic fashion by repeated movements of at least one of the roller 716 and microfluidic device 700 with respect to the other.

In general, the total volume of the mixtures formed by the combination of reagents 735i in the N channels of device 700 includes at least about 70% (e.g., at least about 80%, at least about 90%, at least about 95%, essentially all) of the amount of liquid sample introduced to the device 700. In an exemplary embodiment the total volume of the mixtures formed by the combination of reagents 735i in the N channels of device 700 includes at least about 90% of the amount of liquid sample introduced to the device 700.

Within each mixture of the microfluidic device, particles, if present, combine with detectable label to form complexes. After a suitable incubation period to permit complex formation, the presence of complexes is detected. Each reagent 735i is typically configured to permit detection of a different analyte. Examples of detection of complexes are described in International Patent Application PCT/EP2006/068153, which is incorporated by reference in its entirety.

Figure 10F:
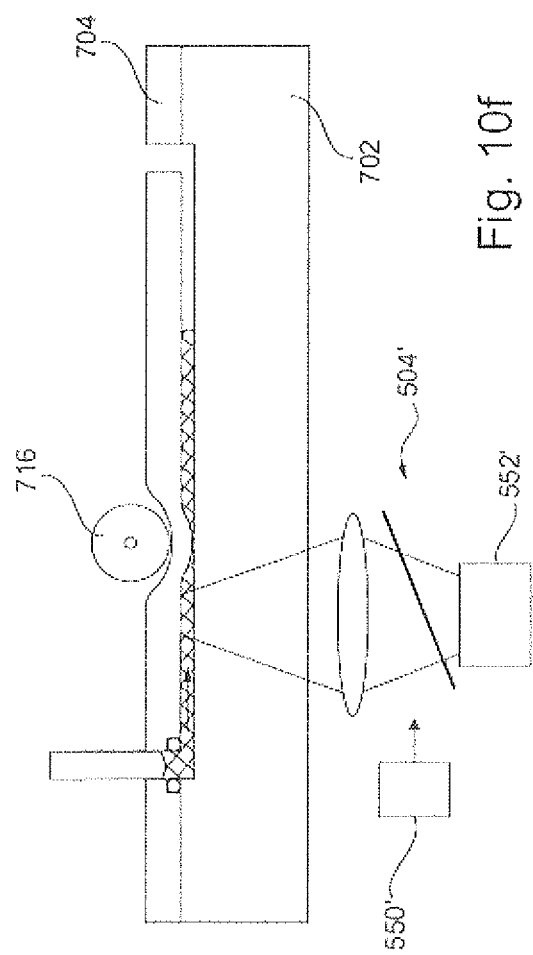
FIG. 10f illustrates the microfluidic device of FIG. 10e and detection of an analyte present within a portion of the liquid sample.

Referring to FIG. 10f, detection typically takes place within a subset of each mixture within the device. In general, detection can be performed within multiple different subsets of each mixture. For example, different subsets of each mixture can be moved through the detection zone by moving roller 716 in a compressed state to move a fresh portion of the mixture into each detection zone. This can be performed multiple times so that substantially all (e.g., at least 70%, at least 80%, at least 90%, at least 95%, essentially all) of each mixture can be subjected to detection. In this embodiment, detection is performed with roller 716 in a compressed state. Mixture that has already been subject to detection enters capillary 736, which acts as a waste container.

In some embodiments, detection is performed by scanning the device 700 with respect to the optical detector so that each detection sequentially comprises a different subset of the solution. This can be performed multiple times so that substantially all (e.g., at least 70%, at least 80%, at least 90%, at least 95%, essentially all) of each mixture can be subjected to detection. In this embodiment, detection is performed with roller 716 in a decompressed state.

In some embodiments, a structure, e.g. microfluidic channel, of the devices or systems described herein can include a capillary comprising a matrix. Accordingly, the methods described herein can be based on the use of structures, e.g. microfluidic channels, which include a capillary comprising a matrix.

In some embodiments, the term "matrix" as used herein refers to a filling or scaffold material which may be within capillary structures such as the capillary inlet. The matrix may be a three dimensional substrate or a composition of substrates or reagent medium. Further, the matrix may have an at least partially amorphous and/or at least partially particulate and/or fabric-like and/or texture-like and/or sponge-like structure, for instance including one or more reticulate or polymeric materials. The term "reticulate or polymeric material", as used herein, may be any material having a fabric-like and/or texture-like and/or sponge-like structure that can be used for the manufacture of a matrix. E.g, the matrix may be or include a pellet and/or a filter cake and/or a substance cake and/or a cake wherein the pellet and/or filter cake and/or substance cake and/or cake includes reagents as described herein. However, the term "matrix" as used herein does not denote to a coating of a capillary structure such as a capillary inlet.

In some embodiments, the term "matrix or three-dimensional reagent medium or filling medium or scaffold material" as used herein denotes a medium or material which is fixated in a capillary and/or may be distributed over significant portions of the capillary structure. These portions typically include all areas of a cross section, e.g. they may not only be confined to outer, parietal sections of the capillary structure, but can include also central and near central areas of a cross section through a capillary structure. The matrix may encompass between about 10% and 95%, between about 20% and 75% or about 50% of the inner volume of a capillary structure.

In one embodiment, the matrix extends over the entire cross sectional area of the capillary structure. In a further embodiment, the matrix does not extend over the whole length of the capillary structure. The matrix may accordingly encompass between 5% and 75%, between about 15% and 60% or between about 35% and 50% of the entire length of the capillary structure. In cases in which not the entire length of the capillary structure is filled with the matrix, the matrix may extend over the entire cross sectional area of the capillary structure or comprise only a sub-section of the cross sectional area of the capillary structure, e.g. between about 5 and 95%, 10 and 80%, 25 and 60% or 50% of the cross sectional area of the capillary structure.

In some embodiments, the term "fixate" refers to any chemical binding between the matrix material and the capillary surface, e.g. a covalent chemical binding or an ionic or electrostatic interaction. Alternatively or in addition, a fixation may also be a physical or mechanical binding caused, e.g. by the presence of interlocking units in the matrix material and the capillary structure.

A matrix as described herein may have several properties which allow an efficient interaction with liquids, in particular biological sample liquids like blood, plasma, serum, urine, sputum, lymph fluid, salvia or cerebrospinal fluid, cellular suspensions etc.

Typically, the matrix is wettable. The term "wettable" refers to the possibility of the matrix to allow a penetration with liquid molecules, typically with water molecules or biological samples such as blood samples.

Additionally, the matrix may allow the flow through of liquid, in particular of aqueous liquids or biological sample liquids. The term "flow through" denotes a movement of liquid or sample particles from one opening of a capillary or tube like structure to the other opening. The time necessary for a flow through may depend on the porosity, the individual size of the pores or the density or the cake-like or amorphous or particulate structure of the matrix material. Typically, the matrix or flow-through medium allows a flow through of liquids in a period of time which is increased by between 1 to 1000%, 5 to 500%, 10 to 100%, 20 to 75% or 30% in comparison to the time needed for a flow through of the same liquid in the same capillary structure or tube like structure comprising no matrix.

In one embodiment, the matrix may be at least partially dissolvable in a liquid, e.g. in a liquid biological sample such as blood. The term "dissolvable" denotes the property of the matrix that the entire matrix or sub-portions therefore may be dragged away or carried away after having been brought into contact with a liquid. The term "carry away" relates not only to the breaking off of larger elements of the matrix, but also to the releasing of small, individual molecule-size or atom-size matrix components into the liquid.

Dissolution of the matrix as described herein may be complete or only partial, e.g. only from 1% to 99%, 5% to 90%, 10% to 75%, 20% to 60% or 30% to 50% of the matrix may be dissolved.

The dissolution rate of the matrix may depend on the flow velocity or flow rate of the liquid, the capillary flow properties, the cake-like or amorphous or particulate character of the matrix, the porosity of the matrix, the pore size, the chemical constitution of the liquid, e.g. the pH or ionic/salt concentration in the liquid, the ambient temperature and the like. Furthermore, the dissolution rate may be influenced by turbulences and/or shearing forces and/or swirls in the matrix. All these parameters may be suitably adjusted, e.g. by the design, form, porosity, density, cake-like, amorphous, particulate structure etc. of the matrix as the person skilled in the art would know, in order to optimize the dissolution behaviour.

Furthermore, the dissolution of the matrix may also be influenced by diffusion processes. Such processes may be controlled by adjusting the diffusion rate within the liquid or sample.

In one embodiment, the matrix may also be used in non-capillary tubes. In such a scenario, the dissolution of the matrix material may be enhanced by the use of pumps or the like.

In a further embodiment, the matrix may comprise one or more reagents or components necessary for the processing and/or analysis of samples or analytes. The one or more reagents may be at least partially dissolvable in a liquid, e.g. in a liquid biological sample such as blood. Typically, a matrix comprises a means or reagent for the detection of analytes or sample ingredients and/or a means or reagent for the stabilization of analytes, sample ingredients or components of the matrix and/or a means or reagent for the amelioration of dissolving processes and/or a means or reagent for the inhibition of deterioration of analytes or sample ingredients and/or a means or reagent for lysing cells.

In one embodiment, the matrix may be not dissolvable in a liquid. Such a non-dissolvable matrix may also comprise the one or more reagents or components as described above necessary for the processing and/or analysis of samples or analytes. The one or more reagents may be at least partially dissolvable in a liquid, e.g. in a liquid biological sample such as blood.

A "means or reagent for the detection of analytes or sample ingredients" as used herein may be a detectable label which reacts with the analyte to form a complex including the label, e.g. a labelled antibody, ligand or interactor for the analyte. E.g., an anti-CD4 and/or an anti-CD3 antibody may be used. In embodiments where more than one reagent for the detection of analytes are used the reagents may be provided with distinct labels, e.g. labels having distinct emission wavelengths. A "label" may be any suitable label known to the person skilled in the art, e.g. a fluorescent label like phycoerythrin, Cy3 or Cy5 etc. Examples of labels may be derived from Slavik J. et al. (1994), "Fluorescent Probes in Cellular and Molecular Biology", CRC Publ. or from Horobin R. and Kiernan J. (2002), "Conn's Biological Stains: A Handbook of Dyes, Stains and Fluorochromes for Use in Biology and Medicine", Taylor and Francis, which are all incorporated herein by reference. In some embodiments, a label may be a dye, a particle, a catalyst such as an enzyme or the like.

A "means or reagent for the stabilization of analytes, sample ingredients or components of the matrix" may be, for example, a protein which has blocking capacities like BSA or HSA or a polypeptide fraction of purified porcine skin allergen (cf. P. J. Gaffney et al., J. Pharm. Pharmacol. 1996, 48: 896-898), e.g. Prionex (obtainable by Polysciences, Eppelheim, Germany), trehalose or the like and thus contributes to a reduction of decomposition processes. Furthermore, it may maintain the activity of analytes or components of the matrix during processing steps like, e.g. heat denaturation, lyophilisation or in long-term storage situations.

In some embodiments, a "means or reagent for the amelioration of dissolving processes" as used herein, denotes chemical units like detergents, micelle formers or buffers which may enhance the separation of sample components or their processing and may contribute to a prevention of the attachment of sample components like proteins to the surface of capillary structures. For instance, polysorbate detergents such as Tween 20 may be used as a detergent.

In some embodiments, the term "means or reagent for the inhibition of deterioration of analytes or sample ingredients" as used herein relates to compounds which inhibit processes like, e.g. coagulation of biological analytes or degradation processes. Typically, a matrix may comprise anticoagulants like Hirudin and/or Ticlopidine and/or suitable DNAse inhibitors and/or RNAse inhibitors known to the person skilled in the art.

In some embodiments, a "means for lysing cells" as used herein, denotes reagents which actively break open or lyse cells. Exemplary means for lysing cells are chemical agents like NaOH, $NH_4Cl$ or the like, detergents like saponins, Triton X114, sucrosemonolaureate, sodium dodecylsulfate polyacrylamide (SDS), N-laureyl-sacrosin-sodium salts or the like; and enzymes such as streptolysine, hemolysine or the like. For instance, lysing agents such as saponins may be used which may be more efficient in lysing red blood cells than white blood cells.

The result of the at least partial dissolving of the matrix as described herein above may be a complete or at least partial mixture of analytes or sample ingredients with components of the matrix. Such a mixture may be ready for subsequent assessment, e.g. in a microfluidic channel or detection region being associated with or in contact with the capillary structure or tube-like structure comprising the matrix as defined herein above. The mixture may be formed by capillary flow forces present in the capillary structure, or alternatively or in addition be formed by the use of pumps or similar facilities in a device as described herein.

In a further embodiment, the matrix may comprise freeze-dried components, e.g. be a lyophilisate of reagents as described herein. The term "freeze-dried" refers to the end product of a lyophilisation process which is carried out under low temperatures. Typically, freeze drying works by freezing the material and then reducing the surrounding pressure and adding enough heat to allow the frozen water in the material to sublime directly from the solid phase to gas. The freeze-drying process may be supported by the addition of lyoprotectants which safeguard the preservation of matrix components like, e.g., proteins, labels etc. Typically, lyoprotectants like polyhydroxy compounds such as sugars (mono-, di-, and polysaccharides), polyalcohols, and their derivatives, trehalose or sucrose may be used. During the freeze-drying process further compounds may be used, which, for instance, lead to an amorphous freezing of the matrix components. Typically, a cyclodextrin or derivative thereof such as hydroxypropyl-gamma-cyclodextrine, e.g. Cavasol W8-HP from Wacker Chemie (Germany) may be used for such a purpose.

The freeze-dry process may be carried out with a capillary tube or structure comprising the matrix components. For instance, the matrix components may be present as liquid or near liquid solution before the lyophilisation process starts. The parameters used for the lyophilisation or freeze-dry process may have an influence on the cake-like or amorphous or particulate character of the matrix, the porosity of the matrix, i.e. the pore size and/or density of the matrix. These parameters may be suitably adjusted. Details would be known to the person skilled in the art or can be derived from Kennedy and Cabral (1993), "Recovery Processes for Biological Materials", John Wiley & Sons Ltd which is incorporated herein by reference in its entirety.

Further, the matrix may be at least partially porous. The term "porous" denotes a material comprising in its interior and/or on its surface one or more pores and/or openings. The one or more internal pores and/or openings may be interconnected. The porosity of a material is typically defined as a percentage of the total volume of its voids, i.e. the internal pores and openings, available for fluid transmission to its overall total volume.

The porous material or porous matrix may have a pore size, measured as the pore diameter. The pore size defines the ability of analyte molecules to penetrate inside the matrix and interact with its inner surface. The ratio of the outer surface of a porous material to its inner is typically, for instance, about 1:1000. Surface molecular interactions mainly occur on the inner surface of matrix materials.

Methods for assessing the pore size are known to a person skilled in the art.

For instance, a convenient way to assess internal pore spaces in a material is the "water saturation method". In brief, a known volume of the porous material to be analyzed is incubated with a known volume of water for a defined period of time, for example for a few hours, to ensure that the material is fully saturated with water. Then, the excess (i.e. "unsaturated") water is removed and its volume measured. The volume of the pore space can subsequently be calculated by subtracting the volume of the excess water from the total volume of water originally used for the analysis. The porosity of the matrix may be determined by calculating the ratio of the volume of the pore space, as measured above, and the total volume of the matrix and by multiplying the result obtained with 100%.

Alternatively, the porosity of a material may be determined by (static volume) gas adsorption measurements. The principle of this method is based on the introduction of consecutive known amounts of an adsorbate (i.e. an adsorbable gas) into the sample material starting from high vacuum and increasing step by step the pressure up to the adsorbate saturation pressure. Adsorption of the injected gas by the sample causes the pressure to slowly decrease until an equilibrium pressure is established. The gas uptake can be calculated directly from the equilibrium pressure values but a dead volume calibration has to be performed before or after the measurement by a "blank run" (that is an analysis using an inert gas not adsorbed on the sample in the analytical conditions, most commonly used is helium). The method is further detailed, e.g., in Groen, J. C. et al. (2003) *Micropor. Mesopor. Mater.* 60, 1-10, which is incorporated herein by reference in its entirety.

A further method known as "Capillary Flow Porometry" may be employed in order to assess the porosity of a material. The method is based on a spontaneous filling of porous material with wetting liquids. Subsequently, pressurized gas is used to remove liquids from pores to allow a gas flow. Pressure and flow rates through wet and dry samples can subsequently be used to compute the properties of the analyzed material.

A porous matrix as described herein may have a porosity of at least 30%, 40%, 50%, 60%, 70% or 80%.

Pores of a porous matrix as described herein may have pore diameter of about 0.001 μm to about 40 μm, of about 0.01 μm to about 10 μm or of about 0.1 μm to 5 μm.

The amorphous and/or particulate and/or cake-like structure and/or porosity and/or pore size of the porous matrix may be adjusted in accordance with the nature and ingredients of the sample to be analyzed in a device. E.g., the porosity of a substance cake may be increased with increasing viscosity of the sample. Is, for example, a sample comprising entire eukaryotic cells to be analyzed the pore size of a matrix may be adjusted to a size having at least the size of a eukaryotic cell. Is, on the other hand, a sample comprising phages or virus particles to be analyzed, the pore size may be adjusted to the size of the phages or virus particles etc.

As a complementary property to porosity, a porous matrix may have a density. Typically, the overall density of the material decreases with increasing porosity. E.g., a porous matrix may have a density which is decreased by about 40% to 70% in comparison to the density of the same or a similar material having no pores or openings.

The matrix may be prepared by freeze-drying a solution comprising two types of antibodies labeled with different labels and further comprising substances which ensure the stability of the antibodies. In one embodiment, a typical recipe for such a solution is:

| Substance | Volume/μl |
|---|---|
| Anti-CD4 Antibody (e.g. from Beckton Dickinson, USA), Phycoerythrine-labeled | 0.075 |
| Anti-CD3 Antibody (e.g. from Beckton Dickinson, USA), Phycoerythrine-Cy5-labeled | 0.10 |
| Prionex (Polysciences, Eppelheim, Germany) | 0.25 |
| Cavasol W8-HP, 40% (Wacker Chemie GmbH, Germany) | 0.25 |
| Tween 20, 1% (Merck, Germany) | 0.05 |
| Hirudin, 50 μg/ml (Sigma Aldrich, Germany) | 0.10 |
| Ticlopidin, 5 mM (Sigma Aldrich, Germany) | 0.10 |

The solution may be filtrated by centrifugation through 0.2 μm pores for 2 minutes to remove particles. A degassing step of 1 minute may follow. Thereafter, the solution is ready to be filled into a capillary or capillary inlet or inlet region, e.g. by pipetting.

Filling of a capillary or capillary inlet with a solution may be done as follows. The solution, e.g. in an amount of p.e. 0.925 μl, may be pipetted manually into a plastic capillary which may be coated with EDTA Immediately after that the capillary may be inserted into liquid nitrogen (e.g. in a plastic foam container) to freeze the content rapidly. The capillary may be kept under liquid nitrogen till they can be inserted into the freeze-drier.

Freeze-drying of a capillary or capillary inlet in order to provide the matrix may be done as follows. The capillary may be transferred with the liquid nitrogen into aluminum troughs, and these may be put into the freeze-drier. An exemplary drying cycle starts with 2 hours at −40° C. and a pressure of 0.011 mbar. Then, an additional drying step for 1 hour at 20° C. and a pressure of 0.001 mbar may follow.

At the end of the freeze-drying process the capillaries may be layered onto a drying medium (e.g. silica gel) and then distributed into little containers for storage (e.g. PCR-tubes or upper or lower part of a petri dish). These may be kept in aluminum pouches sealed under argon protection until mounting into the cartridges.

In another embodiment, a typical recipe for a solution which may be freeze-dried in order to prepare a matrix in a capillary inlet is:

| Substance | Volume/μl |
|---|---|
| Anti-CD4 Antibody (e.g. from Beckton Dickinson, USA), Phycoerythrine-labeled | 0.056 |
| Anti-CD3 Antibody (e.g. from Beckton Dickinson, USA), Phycoerythrine-Cy5-labeled | 0.075 |
| Saponin, 15 g/100 ml (Sigma Aldrich, Germany) | 0.25 |
| Trehalose, 1M (Sigma Aldrich, Germany) | 0.10 |
| $H_2O$ | 0.419 |

The solution may be filtrated by centrifugation through 0.45 μm pores for 2 minutes to remove particles. Thereafter the solution is ready to be filled into a capillary inlet, e.g. by pipetting. Filling of the capillaries and freeze-drying of the solution in order to prepare the matrix may be performed as described above.

Methods directed to the introduction of samples or analytes into microfluidic channels and the analysis of the sample or analytes, e.g. by forming of mixtures and/or complexes as described herein above or below may comprise interactions of analytes with the matrix. The interaction may be, for instance, part of methods carried out in open or closed circuit devices or systems. Such methods may include all herein above-mentioned interactions. E.g., the analyte or sample may at least partially dissolve the matrix.

In a further aspect, devices or systems are provided which comprise or are associated with control elements. Further, methods are provided using such control elements or using devices or systems comprising or being associated with such control elements.

The term "control element" or "control feature" relates to a unit or factor which allows the testing, reviewing, examining, scanning, revising or inspecting of a device or system or sub-unit of the device or system as described herein or of a test result or a result of the analysis and also to the possibility to compare, verify and contrast obtained results during and/or after the use of a device or system or during and/or after performing the methods described herein. The term also denotes the performance of such controlling activities within the methods as defined herein above or below.

The term "controlling activity" may accordingly relate to the employment of internal testing or control elements or factors, which may be present within the device or system and/or must not added externally. Particularly, such internal control elements may allow a real-time and/or in situ checking of parameter without any need of recurring to external, separate and/or time-delayed controls.

In one embodiment, a device or system may comprise analytes or analyte analogues being immobilized within the microfluidic channel. In some embodiments, the term "analyte analogues" as used herein denotes an entity or compound or substance having the same or essentially the same binding behavior or reactivity, e.g. binding affinity, as the analyte to be examined with respect to a label or probe compound or capture molecule which is used for detection of the analyte to be examined. The analytes or analyte analogues being immobilized within the microfluidic channel may be particles. The term "particle" refers to a physical, chemical or biological entity, which may be identical or similar to an analyte to be examined. A particle may, for instance, be a cell, e.g. a cell showing a specific antigen, e.g. the same antigen as the analyte to be examined. An analyte analogue may be a bead showing a specific antigen, e.g. the same antigen as the analyte to be examined. The term "immobilization" means that the particle is fixated in the microfluidic channel, e.g. by chemical or mechanical means in way that at least the surface structure, in particular the conformation and identity of surface proteins, is not modified or at least still allows a specific interaction with binding detection moieties like antibodies or ligands. Such an immobilized particle, e.g. an immobilized eukaryotic cell, T-cell or monocyte may be present in the microfluidic channel in predefined and/or known amount or concentration and/or at a predefined or known position. The amount of such particles, in particular cells, may be much higher than the amount of comparable analytes in the sample to be examined. Furthermore, the particles may be concentrated at a certain predefined or known spot or position of the microfluidic channel allowing for a rapid and easy verification of interaction with corresponding labeled interactors. The particles may subsequently be used for a control test aiming at the verification of labeling processes as defined herein below.

The term "controlling activity" may also refer to the practical testing of the device or system, e.g. in terms of malfunction of the entire device or system or sub-portions or elements thereof. For example, several control items of the device of system may be separately addressed and checked.

In one embodiment, such a control may involve the testing of labeling reactions and/or the presence of cells in a sample to be analyzed with the help of immobilized particles, e.g. immobilized cells, as defined herein above. The particles may be labeled or treated with labels similar or identical to the analytes to be detected or examined. Due to the known position and number of the immobilized particles it can be verified whether the labeling reaction was successful. The presence of a label may be tested with the help of appropriate chemical, optical or electronic measurement instruments or sensors, as known to the person skilled in the art.

Should the test result in a lack of, e.g. fluorescence emissions or a reduction of the emission value in comparison to a predefined known value after an appropriate elicitation, it may be concluded that the labeling process was not successful. The device may accordingly be stopped and/or the test(s) and/or the image(s) may be marked as invalid.

Should the test result, on the other hand, in a detectable, in particular validly detectable signal from the immobilized particles, whereas the co-treated analyte and/or sample does not provide any signal, it may be concluded that the analyte and/or sample does not comprise structures which would have allowed an interaction with the label, e.g. a labeled antibody. For example, if a labeled anti-CD4 or anti-CD3 antibody is used, a lack of emission signal from the sample, although the immobilized particles, e.g. immobilized T-cells, provide a signal, may be seen as an indication for the fact that no CD4- and/or CD3-bearing cells or components are present in the sample to be examined.

In a specific embodiment, the immobilized particles may be concentrated at a certain predefined or known spot or position of the microfluidic channel. Such a concentration of the particles may give rise to a strongly increased emission signal. Due to the increased intensity of the signal and its concentration in comparison to a signal derivable from an individual analyte, e.g. one cell, there will be no superimposition of the signals derivable from the immobilized particles and the examined analytes.

Immobilized $T_H$-cells (i.e. T helper cells) may be used as positive controls in order to evaluate the function of the different reagents used in the assay. In some embodiments, immobilized $T_H$-cells may be included in a fraction of immobilized mononuclear cells (MNC). Such mononuclear cells can be obtained, for instance, from a full blood sample using a density gradient centrifugation step. In some embodiments, $T_H$-cells for immobilization can be obtained, for instance, from an in vitro cell culture.

In the following, a typical protocol for preparing $T_H$-cells from a whole blood sample is described.

Four milliliters of Histopaque-1077 (Sigma Aldrich) may be filled into centrifugation tubes, heated to 18-20° C. and covered with 4 ml of an EDTA full blood sample. The centrifugation tubes may be placed in a centrifuge and spinned 30 min at 400 g at room temperature. After centrifugation, the upper layer may be discarded and the fraction containing the mononuclear cells may be transferred into a new reaction tube. For washing, the cells may be resuspended in PBS, followed by a centrifugation step for 10 min at 250 g. The supernatant may be removed and the pellet may be resuspended in PBS. Washing may be repeated one to several times.

In some embodiments, the number of cells in the solution may be adjusted for the following spotting procedure. For this purpose, a typical cell count procedure, using e.g. a Beckton Dickinson FACSCalibur, may be performed according to the device manufacturer's instructions.

In some embodiments, for immobilizing the cells the number of cells may be adjusted to a number from 2,000/µl to 20,000/µl, from 5,000/µl to 15,000/µl, or from 7,500/µl to 12,500/µl or about 10,000 µl.

In some embodiments, phosphate buffered saline (PBS) may be used for adjusting the cell number to a desired value.

In some embodiments, the cells are immobilized via spotting onto the surface. Such a spotting solution may be prepared by resuspending cells in PBS, for instance, in a concentration of around 10.000 cells per µl.

In some embodiments, one or more drops of the spotting solution may be transferred to a surface, for instance, on the bottom of the detection region of a device as described herein. For instance, 1, 2, 3, 4 or 5 or more spots are spotted onto the surface. In some embodiments, 1, 2 or 3 drops á 100 nl cell suspension may be transferred to the surface. Further, the drops may be spotted directly adjacent to each other, e.g. in such a manner that they flow together after spotting.

In some embodiments, the surface for spotting positive controls such as T helper cells may be treated before spotting. For instance, plasma treatment of the surface may effect the hydrophobicity of the surface. In some embodiments, a hydrophilic surface for spotting may be used.

In some embodiments, drying of the spotted cells takes place at ambient conditions.

In addition or alternatively, other methods for immobilizing cells such as those described in U.S. Pat. No. 6,008,052 can be used. For instance, a dried mammalian cell may be used as a reference particle in an immunoassay whose light scatter properties are substantially unaltered upon rehydration and whose autofluorescence does not increase with time wherein the cell has been fixed with a fixative, reduced with a Schiff's base reducing agent and then dried in the presence of a protein stabilizing compound.

In some embodiments, a further control may involve the checking of the detection, e.g. cell count plausibility on the device or assessment system. The test may be based on the detection of the presence of certain target analytes, e.g. T-lymphocytes. For instance, it may be checked whether the number of T-cells is higher than the number of monocytes (i.e. the amount of detectable markers CD3+CD4+ and CD3+ CD4− must be elevated in comparison to CD3−CD4+). The test may preferably be performed after a verification of the labeling reaction as defined herein above has been successful finished. The checking may be carried out, e.g. with the help of appropriate chemical or biochemical marker or label reagents and optical and/or electronic sensors as well as well as suitable software applications known to the person skilled in the art. The test may be performed after a label reaction as described herein above or below has been carried out. Should the test result in an inaccurate or invalid number of target analytes, e.g. T-lymphocytes the use of the device may be stopped and/or the test(s) may be marked as invalid.

A device or system as described herein may further include several elements or components or technical modules such as motors, light sources such as LEDs, interfaces, processors, data storage units, optical systems, barcode or datamatrix readers, internal or external power supplies, pumps, actuators, electronic parts etc. Controls may be directed to the testing of the various elements or technical modules.

In some embodiments, a control may be directed to the testing of a motor of the device or system as described herein. A motor check may be carried out. In this context, a reference position may be checked by testing the move of end-switches to axis reference positions. The checking may be carried out with the help of appropriate mechanical, optical or electrical/electronic sensors as known to the person skilled in the art, which allow a measurement of the movements. Should the test result in an inaccurate positioning the use of the device may be stopped.

Furthermore, a movement control of the motor may be carried out by testing the smooth running on all axes of the device or system. The checking may be carried out with the help of appropriate mechanical, optical or electrical/electronic sensors as known to the person skilled in the art, which allow a measurement of the movements. Should the test result in an inaccurate accurate moving behavior of the device may be stopped.

A further control may involve the checking of current overload of the motor. The checking may be carried out, e.g. with the help of appropriate software as known to the person skilled in the art. The current overload of the motor may also be checked via the functionality of a motor fuse. The checking may be carried out, e.g. with the help of appropriate software as known to the person skilled in the art. Should the test result in inaccurate loading or overloading the device may be stopped.

A further control may involve the checking of LED currents. The checking may be carried out, e.g. with the help of appropriate mechanical, optical or electrical/electronic sensors as known to the person skilled in the art, which allow a measurement of the LED current. Should the test result in inaccurate LED currents the device may be stopped.

A further control may involve the checking of filter element positions and changeability by assessing the centering of the filter elements along the optical axis. The checking may be carried out, e.g. with the help of appropriate mechanical, optical or electrical/electronic sensors as known to the person skilled in the art. Should the test result in inaccurate filter positioning or changeability the device may be stopped.

A further control may involve the checking of hardware elements by assessing start- and stop-bits. The checking may be carried out, e.g. with the help of appropriate software as known to the person skilled in the art. Should the test result in an inaccurate presence of start- or stop-bits the device may be stopped.

A further control may involve the checking of barcodes on a device by assessing parity values. The checking may be carried out, e.g. with appropriate optical and/or electrical/electronic sensors as known to the person skilled in the art. Should the test result in an inaccurate parity, the device cannot be read and may be stopped.

A further control may involve the checking of power supply voltage. The checking may be carried out, e.g. with the help of appropriate electrical or electronic sensors as known to the person skilled in the art. Should the test result in an inaccurate power supply, the device cannot be started and may be stopped.

A further control may involve the checking the battery charge. The checking may be carried out, e.g. with the help of appropriate electrical or electronic sensors as known to the person skilled in the art. Should the test result in an inaccurate battery charge, the device cannot be started with a battery and may be stopped. Alternatively, the user may be prompted to recharge the battery or replace it.

A further control may involve the checking of storage capacity on the device assessment system. The checking may be carried out, e.g. with the help of appropriate software as known to the person skilled in the art. Should the test result in an inaccurate or insufficient storage capacity, the user may be prompted to delete files on the system and/or the device may be stopped.

A further control may involve the checking of date plausibility on the device assessment system. The checking may be carried out, e.g. with the help of appropriate software as known to the person skilled in the art. Should the test result in an inaccurate date or a date younger than the date of the last software update, the user may be prompted to check the system and/or to input the current date and time and/or the device may be stopped.

A further control may involve the checking of the device temperature. The checking may be carried out, e.g. with the help of appropriate physical or electronic temperature measuring instruments as known to the person skilled in the art. Should the test result in an inaccurate temperature, the user may be prompted to switch off the device or the device may be stopped.

A further control may involve the checking of the contact of a pressure tube pump by adjusting the tube pump roll to ensure that the tube is squeezed with a defined force. The checking may be carried out, e.g. with the help of appropriate mechanical, optical or electrical/electronic sensors as known to the person skilled in the art. Should the test result in an inaccurate function of the pressure tube pump the device may be stopped and/or the test(s) may be marked as invalid.

In a specific embodiment, a control may involve the checking of the focus of the scanning unit of a device or system as described herein by detecting optically distinguishable beads present in the microfluidic channel. The beads may be immobilized in the microfluidic channel by chemical or mechanical binding to the channel surface. For instance, the beads may be bound by covalent chemical binding to the channel surface or by the use of mechanical interaction due to interlocking units. The beads may not be movable or removable by liquid flow through the channel. The beads may be labeled with a fluorescent label as defined herein above. The beads may have any suitable form or be of any suitable type know to the person skilled in the art. Examples of such beads are latex beads labeled with a fluorescent dye. The label used for the labeling of the beads may be the same label used for the labeling of compounds being able to bind to analytes or samples as described herein, e.g. antibodies or ligands etc. as defined herein above, or alternatively a different label. The emitted wavelength after excitation may be identical or different in comparison to the wavelength emitted by labels associated with or binding to analytes or samples to be examined. The emitted light may be stronger than the light emitted from labels associated with or binding to analytes or samples to be examined. The emitted light may accordingly be detected based on a shorter exposure time. The number and localisation of beads and the intensity of light emission of the beads may be known and/or predefined. By comparing these parameters after an autofocus process has been finished it may be verified whether the scanning unit is in focus. Should the test result in an inaccurate focus of the scanning unit the device may be stopped and/or the test(s) may be marked as invalid.

In a further embodiment, a control element includes a means for determining of a fluorescence background in the microfluidic channel. The term "means for determining a fluorescence background" relates to optical and/or electronic sensor or measurement systems as well as appropriate image analysis software which allow the detection of fluorescence signals in zones or areas of the microfluidic channel, in which no analyte- or particle-associated emission is detectable. Labeling reactions etc. have been described in the context of the testing of the labeling reactions herein above.

Any obtained value may subsequently be used for a subtraction of the background fluorescence from the measured analyte-associated emissions in order to allow a normalization of the signals and to improve the accuracy of the measurement.

A further control may involve the checking of the focus range of the scanning unit of a device or system as described herein by detecting optically distinguishable beads present in the microfluidic channel as defined herein above. The checking may be carried out by determining whether the focus position is at the edges of the operating range of the autofocus servo. Should the test result in an inaccurate focus range of the scanning unit the device may be stopped and/or the test(s) may be marked as invalid.

A further control may involve the checking of the exposure time for the detection of light emission. The test may be carried out by verifying whether automatically adapted exposure times lead to exposure times that a within a predefined range. Should the test result in an inaccurate exposure time, the device may be stopped and/or the test(s) may be marked as invalid.

In a further embodiment, a means for the detecting the filling of the microfluidic channel is provided. Typically, such means are optical or electronic sensors, e.g. a CCD camera, a light barrier and the like, connected to a suitable computer system and image processing software as known to the person skilled in the art which allow monitoring channel openings. A corresponding control may be carried out by validating the outflow hole of a microfluidic channel via the comparison of the properties of images of the outflow hole. These properties may change when the hole is filled in comparison to an empty hole. Should the test result in an inaccurate filling of the microfluidic channel the device may be stopped and/or the test(s) may be marked as invalid.

A further control may involve the testing of the filling of device compartments or sub-units with the help of optical or electronic sensors, e.g. CCD camera and the like, connected to a suitable computer system and image processing software as known to the person skilled in the art which allow monitoring channel openings. A corresponding control may be carried out by validating the liquid level of device compartments or sub-units via the comparison of the properties of images obtained from the device compartments or sub-units. These properties may change when the device compartment or sub-unit is filled in comparison to not filled or not entirely filled device compartment or sub-unit. Should the test result in an inaccurate filling of the device compartment or sub-unit the device may be stopped and/or the test(s) may be marked as invalid.

A further control may involve an outlier analysis of images obtained by using the device or system as described herein. The control may be based on the assessment of all or the majority of images obtained during one or more use cycles for outlier images. The assessment may be based on interquartile ranges with the following parameters: (Q1−1.5*IQR)<feature value<(Q3+1.5*IQR). Should the analysis result in an inaccurate outlier analysis value the device may be stopped and/or the test(s) and/or the image(s) may be marked as invalid.

A further control may involve the testing of image intensities by assessing the minimum intensity of red and green color channels. The checking may be carried out, e.g. with the help of appropriate optical and/or electronic sensors or measuring instruments as known to the person skilled in the art. Should the analysis result in inaccurate image intensities in the red and/or green channel the device may be stopped and/or the test(s) and/or the image(s) may be marked as invalid.

A further control may involve the testing of volume present in the microfluidic channel by using appropriate optical, mechanical and/or electric/electronic sensors or measuring instruments as known to the person skilled in the art. In some embodiments, the volume should be in a range from 0.1 to 5 μl, 0.5 to 3 μl, 1 to 2 μl or above 1.25 μl. The liquid to be measured may be blood. Should the analysis result in inaccurate volume present in the microfluidic channel, the device may be stopped and/or the test(s) may be marked as invalid.

In a further embodiment, the volume tested or check as described above may be cross-calculated with the help of a means for determining the volume of the detection channel. Such a means may, for example, be a bar-code or other digitalized readable information tag present on a device or system, which indicates a volume factor or a deviation from a predefined volume for the microfluidic channel. Is, for example, the real microfluidic channel volume different from a typical volume predefined for a microfluidic channel, this information may be derived from a barcode or digitalized readable information tag present on a device or system and used for an adjusted assessment of volume values obtained by a testing procedure as described herein above. Furthermore, the information on the exact volume of the individual microfluidic channels may be used for a very accurate determination of analyte concentration in the sample to be examined, since no average volume values are to be used, but individually determined values. Thereby the exactitude and fidelity of the determination method may be significantly increased.

The term "inaccurate" as used herein means that the measured value for movements, positions, presence of items or signals etc. deviate from a predefined or known value or range of values or a value or range of values indicated as being permissible herein above by at least 0.5%, 1%, 2%, 3%, 4%, 5% %, 6%, 7%, 8%, 9%, 10%, 15%, 20%, inter alia depending on the kind of control. E.g., a value for the expiration date is deemed to be inaccurate if the deviation is more than 0%.

Any of the above mentioned control activities or uses of control elements may be included in method steps as defined herein above or below. For instance a detection method as defined herein or in the claims may comprise additionally any of the control steps mentioned above.

In a further embodiment, the control elements and/or controlling activities may also be used within or for the testing of capillaries or capillary structures as defined herein above. For instance, the charge and structure of the matrix in the capillary may be tested in accordance with a testing scheme for the filling of device compartments as defined herein above.

In a further embodiment, a device or system as described herein, for instance a test cartridge, may be asymmetric, e.g. by having specific alignment structures like asymmetric holes, cropped angels, preferably one, two, or three cropped angles. The asymmetry of the device may be used in order to eliminate misusage or malpositioning of the device with respect to, e.g. a scanning system. Typically, the device may only be entered into the scanning system if properly placed, i.e. if the asymmetry is detected by the scanning device. The asymmetrical elements of the device may be adapted to the form and format of scanning devices known to the person skilled in the art.

In a further embodiment, a sample, e.g. of blood, to be analyzed may be obtained from a patient through a standard fingerstick or venous blood draw. Fingerstick blood may be applied directly to a device or be applied to a capillary inlet or structure, which may be subsequently connected with the device or system as described herein. A small sample volume is preferred for fingerstick use, since it may avoid the possibility of under-filling the receptacle structure, e.g. a capillary in the sample port. Excess liquid may not necessarily be wiped off the capillary. Alternatively, venous blood may be applied to the device by using a pipette. Preferably, fingerstick samples are applied immediately to the cartridge. When obtaining a sample, e.g. of blood, the first sample, e.g. blood drop may be wiped off and the second sample, e.g. blood drop may be obtained without any squeezing After applying the sample, the cap may be snapped into place, in order to eliminate the chance of sample spillage or contamination of the instrument.

Methods and devices for performing assays have been described. Examples of other embodiments are discussed next.

While inlet 106 in FIGS. 1 and 2 has been described as an unobstructed opening, other configurations are possible. For example, an inlet may be configured with a syringe fitting (e.g., a gas-tight fitting) to receive a syringe. Alternatively, an inlet may be configured as a gasket through which a sample may be introduced by a needle. As another alternative, the inlet may be fitted with a one-way valve that allows sample to be introduced but not to exit. As another alternative, the inlet may be configured to receive a standard capillary (e.g., an end-to-end capillary such as a plastic capillary). The capillary may be anti-coagulant coated such as with heparin. Examples of suitable capillaries include 20 μl heparin coated capillaries available from Kabe Labortechnik (Nürnbrecht-Elsenroth, Deutschland; http://www.kabe-labortechnik.de/index.php?sprache=de&akt_seite=startseite_produkte.php).

While a microfluidic device has been described that fills by capillary action, other embodiments can be used. For example, system 500 can be designed to reduce an internal volume of the microfluidic network prior to application of the sample to the inlet. When the sample is applied, the internal volume is increased thereby drawing the sample in. Such a volume decrease can be accomplished with, for example, compression roller 516. For example, microfluidic device may be received within housing 500 so that damped spring 514 of translation actuator 512 is in a compressed state. Compression roller 516 is positioned to compress device 100 at a location corresponding to reservoir 108. This compression reduces an internal volume of reservoir 108. The volume reduction is about as great as (e.g., at least about 25% greater than, at least 50% greater than) the volume of sample to be received within device 100. With reservoir 108 in the compressed state, a volume of sample is applied to inlet 106 of device 100. Compression roller 516 is retracted away from inlet 106 toward an opposite end 137 of device 100. As roller 516 moves away from reservoir 108, the reservoir decompresses thereby increasing the internal volume of the microfluidic network. The volume increase creates a vacuum that sucks the sample into the device.

While microfluidic devices having an open capillary channel have been described, other embodiments can be used. For example, the channel may include a medium occupying at least some (e.g., most or all) of the cross section of the channel along at least a portion of its length. Typically, the medium is one which to multiple probe compounds can be immobilized to define respective spaced apart test zones (e.g., capture volumes), each having capture sites disposed in three dimensions. Pores or voids in the medium permit liquid to permeate along the channel (e.g., by capillary action). Liquid movement along the channel may be assisted by or induced by, for example, generating a vacuum within the channel as described above. Typically, probe compounds are immobilized with respect to the porous medium to define spaced-apart test zones along the channel. Interaction of analytes with probe compounds of the test zones can be determined sequentially as described for test zones 112$i$ of device 100. Because each test zone is disposed in three dimensions, reducing the distance between the opposed inner surfaces of the channel decreases the capture volume occupied by the immobilized probe compounds of the test zone. Optical detection is performed with the test zone in the reduced volume (i.e., reduced distance) state.

Figure 7:
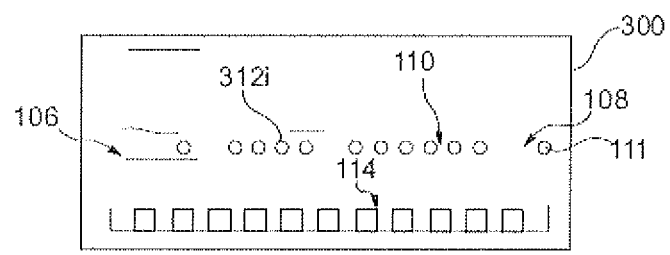
FIG. 7 illustrates a microfluidic device.

While test zones 112$i$ have been shown as elongate, other configurations are possible. For example, referring to FIG. 7, a microfluidic device 300 includes multiple test zones 312$i$ each having a generally circular configuration. Other than a difference in shape, test zones 312$i$ may be identical to test zones 112$i$ of device 100. Other than a difference in test zones, devices 100 and 300 can be identical.

While a method for forming test zones 112$i$ has been described as moving distal tip 404 and substrate 102 from an initial separation d1 (FIG. 3$b$) to an adjacent separation d2 (FIG. 3$c$) and to an intermediate separation d3 (FIG. 3$d$) prior to initiating lateral movement of distal tip 404 and substrate 102 (FIG. 3O, other embodiments can be performed. For example, distal tip 404 and substrate 102 can be moved laterally with tip 404 and substrate 102 in the adjacent separation d2. In this embodiment, separation d2 is typically greater than zero.

While a method for forming test zones 112$i$ has been described as including a step of maintaining distal tip 404 and substrate 102 at an intermediate separation d3 for an incubation time until only a remaining portion 402' of reagent solution 402 remains, other embodiments can be performed. For example, lateral movement of distal tip 404 and substrate 102 can begin immediately as distal tip 404 and substrate 102 are moved from adjacent separation d2 (FIG. 3$c$) to separation d3 (FIG. 3$d$). In other words, the incubation time may be indistinguishable from zero. As another example, during the incubation, evaporating reagent solution may be replaced with additional reagent solution introduced to the capillary tip. Accordingly, the total amount of reagent at the capillary tip increases during the incubation.

While a method for forming test zones 112$i$ has been described as including an incubation time with distal tip 404 and substrate 102 maintained at a separation d3, other embodiments can be performed. For example, separation d3 can vary during the incubation time. For example, tip 404 can be oscillated laterally and or vertically relative to substrate 102 during the incubation time. Alternatively or in combination, tip 404 can be oscillated laterally and or vertically relative to substrate 102 during lateral movement. Such oscillation can enhance transport of probe molecules to the first substrate during incubation or lateral motion.

While a method for forming test zones 112$i$ has been described as using a capillary dispenser, other dispensers may be used. For example, material may be dispensed from a solid dispenser (e.g., a solid rod).

While a method for forming test zones 112$i$ has been described as introducing an amount of reagent solution to a distal tip of a capillary of a capillary spotter (FIG. 3$b$) and bringing the tip and a substrate to a smaller separation d2 so that reagent solution 402 contacts a location of substrate 102, other embodiments can be performed. For example, reagent solution may be introduced to the distal tip only after the distal tip and substrate are brought to a smaller separation (e.g., after the distal tip is contacted with the substrate).

While a method and microfluidic device reader for sequentially reducing a distance between inner surfaces of a channel having been described, other configurations are possible. For example, a microfluidic device reader may be configured to simultaneously reduce a distance between inner surfaces along most (e.g., substantially all or all) of a channel. Subsequently, the reader translates the detection zone of a detector along the channel so that different test zones are read sequentially.

While a microfluidic device having a first relative rigid substrate and a second relatively flexible substrate has been described, other embodiments can be used. For example, the substrates define both opposed inner surfaces of a channel can be flexible. In such embodiments, a portion of the optical detector can form part of the compression system. For example, the microfluidic device may translate between a compression roller and an optic of the detector.

While a reference pattern has been described as providing information related to spatial properties of test zones of a microfluidic device, the reference pattern may provide additional or alternative information. For example, a reference pattern can provide information related to physiochemical properties of test zones of a microfluidic device. Such properties include analytes for which the test zones are configured to assay. Other properties include the identity and properties of reagents stored on the device and date information (e.g., the expiration date) of the device.

While a reference pattern including magnetic indicia has been described, other indicia can be used. For example, the indicia may be formed of regions having different optical density or reflectance as compared to the surrounding material. The reference pattern reader is an optical reader typically configured to read the indicia by transmittance or reflectance.

In other embodiments, the first substrate can include a channel formed, for example, via injection molding. The channel has a first dimension (length) substantially greater than its second and third dimensions (i.e., width and depth). The channel can have a cross section that is rectangular, V-shaped (triangular), U-shaped, or other shape. In some embodiments, the shape and/or dimensions of the cross section of the channel can vary along the length of the channel. The second substrate can be affixed to the first substrate by an adhesive. The second substrate can be formed of, for example, a transparent tape. The second substrate (e.g., the tape) can have a mechanical stiffness, such that mechanical contact with an outer surface of the second substrate (e.g., the tape) does not substantially deform the inner surface of the second substrate.

In certain embodiments, the channel may be defined by the inner surface of a tube, a pipe a capillary or the like. The channel can have a cross section that is rectangular, V-shaped (triangular), or other shape. In some embodiments, the shape and/or dimensions of the cross section of the channel can vary along the length of the channel A portion of the channel may be optically transparent.

In some embodiments, the channel includes one or more reference and/or alignment marks, such as defined structures or immobilized molecules configured to be detectable with the detection system used for the assay. The alignment marks can include, for instance, immobilized fluorescent beads, immobilized fluorescent polymers, proteins, nucleic acids and the like. Alignment marks also can include physical structures like microstructures and the like.

The device can be configured to form a fluid circuit after having introduced the sample to the channel. The fluid circuit encloses the liquid sample in an endless loop. When the liquid sample is enclosed in the fluid circuit, and the volume of the liquid sample is less than the total volume of the fluid circuit, the remaining volume in the fluid circuit can be occupied by a transport fluid. The transport fluid can be a liquid that is substantially immiscible with the sample liquid (e.g., by virtue of hydrophilicity/hydrophobicity, or differences in density). The transport fluid can be a gas, such as, for example, air. Typically, the liquid sample will be present in the fluid circuit in a continuous slug.

A portion of the fluid circuit includes a compressible zone. The compressible zone can be a length of the fluid circuit along which at least one wall of the circuit is compressible or deformable. When a localized compressive force is applied to the compressible zone, the wall deforms. Under a sufficient force, the wall can be compressed to a degree that interrupts the fluid circuit. Most commonly, the fluid circuit will be interrupted at a predetermined location, where the channel is filled with the transport fluid.

Once the fluid circuit has been interrupted, the location of the fluid sample within the fluid circuit can be manipulated by moving the location of the interruption with respect to the rest of the fluid circuit. Moving the interruption decreases the volume of the transport fluid to one side of the interruption, with a corresponding increase in volume of the transport fluid on the other side of the interruption. The changes in volume result in a differential pressure on the ends of the liquid sample (i.e., where the liquid sample and transport fluid meet). The liquid sample responds by moving within the fluid circuit to equalize the pressures.

One or more test zones can be spaced apart along the channel. Typically, each assay includes interaction of the probe compound with the respective analyte or with a respective complex including the analyte and a reagent (e.g., an optical label).

Location of the sample within the channel can be controlled by an actuator or roller configured to subject a portion of the compressible zone to a localized compressive force. The microfluidic device is translated relative to the actuator or roller so that the sample travels to a desired location within the channel. Alternatively, the roller can be moved while the device remains stationary.

Figure 12:
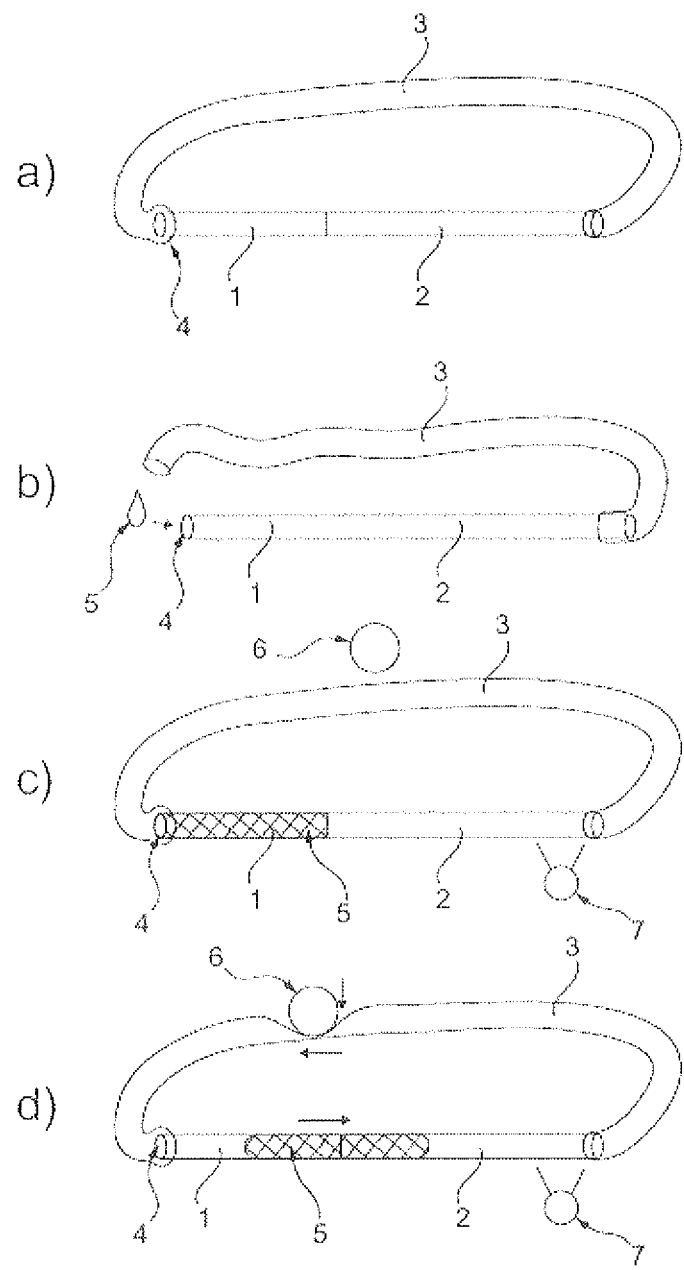
FIGS. 12A-12D show a schematic depiction of a fluid circuit.

FIG. 12A illustrates fluid circuit 10 in a closed state. Fluid circuit 10 includes first zone 1, microfluidic channel 2, second zone 3, and inlet 4. In some embodiments, first zone 1 includes a matrix or substance cake. In the closed state, second zone 3 is tightly connected to inlet 4. FIG. 12B shows fluid circuit 10 in an open state and ready to accept liquid sample 5 at inlet 4. After liquid sample 5 is contacted to inlet 4, capillary action draws liquid sample 5 into first zone 1. FIGS. 12C-12D shows the fluid circuit in a closed state after the sample has been applied. Roller 6 is positioned with respect to second zone 3 such that the second zone is either in an uncompressed state (as in FIG. 12C) or in a compressed state (as in FIG. 12D). The location of liquid sample 5 within fluid circuit 10 can be adjusted by positioning roller 6 such that second zone 3 is in a compressed state, and while maintaining the compressed state, moving roller 6 relative to second zone 3 (illustrated by arrows in FIG. 12D). Because the fluid circuit is closed, the movement of roller 6 creates a differential pressure on either side of the roller; the differential pressure induces movement of liquid sample, thereby restoring equal pressures. The fluid circuit can be configured to work in a cartridge. In certain examples, the fluid circuit can have a microfluidic flow path capable of compression through deformation, a microfluidic channel including a detection region, and a sealing member that can reversibly or irreversibly form a closed fluid circuit.

Figure 13:
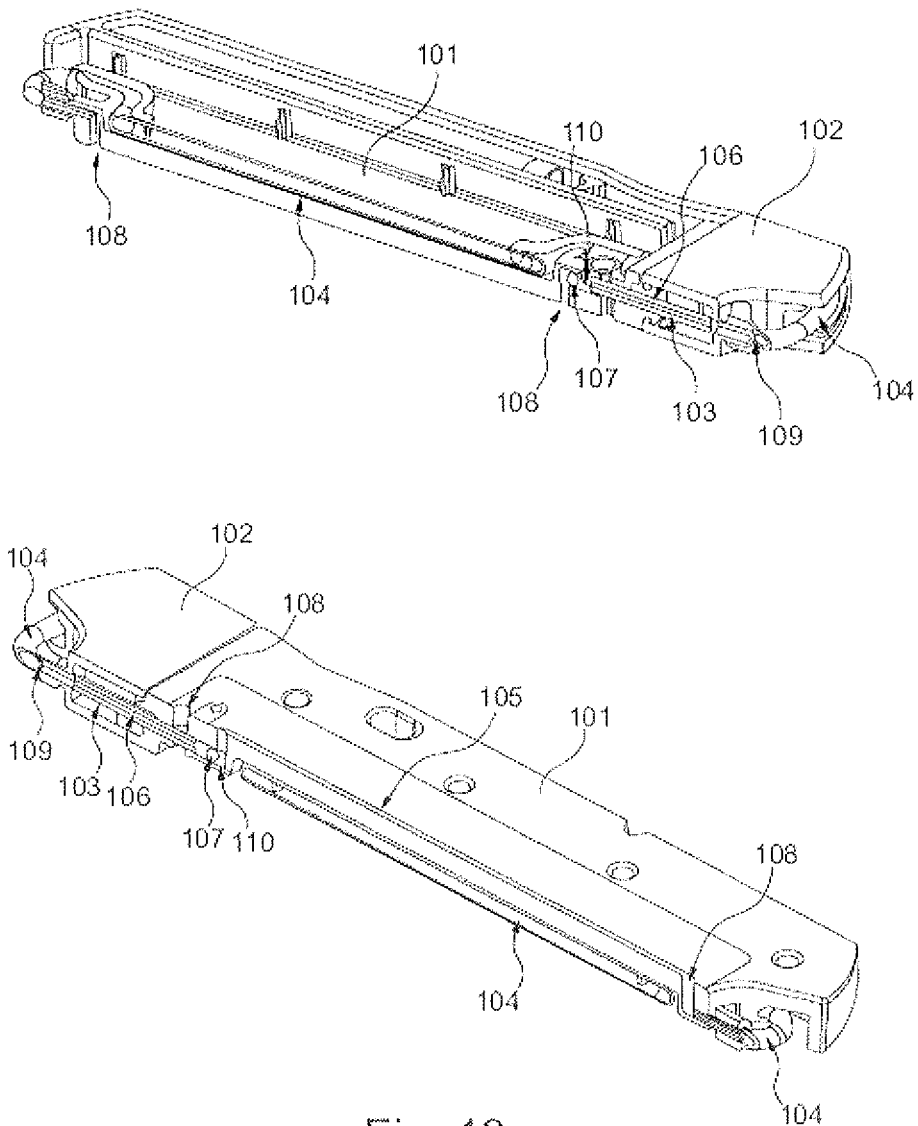
FIGS. 13A-13B show cutaway views of a cartridge having a fluid circuit.

FIGS. 13A-13B show a cutaway views of an exemplary cartridge 100. Cartridge 100 includes substrate 101, cap 102, and a fluid circuit including first zone 103, conduits 108, channel 105, second zone 104, and inlet/tight connection 109. Channel 105 can be covered by an at least partially optically transmissible layer. First zone 103 can be e.g. a capillary, selected to hold a desired sample volume (e.g., 1 µL to 20 µL, 2 to 10 µL, or about 5 µL). The capillary can be coated with an anticoagulant on its inner surface. Inlet 109 of the capillary is configured to receive the sample 106. In some embodiments, the exit of the capillary opens out to a reaction chamber 110 with a predetermined volume of, e.g., about 5 µL, 10 µL or 20 µL. In some embodiments, reaction chamber 110 includes a reagent pellet 107. The reagent pellet can include antibodies labelled with a fluorescent dye and having an affinity for antigens to be detected within the sample. For instance, for detecting the number of T-helper-cells in a liquid sample the reagent pellet can include an anti-CD4+-antibody labelled with a first fluorescent dye (such as phycoerythrine) and an anti-CD3+-antibody labelled with a second fluorescent dye such as (phycoerythrine-Cy5), salts and stabilizing reagents etc. In some embodiments, the inner surface of the first zone is covered with reagents necessary for processing the sample. An exemplary assay for detecting particles such as cells in a liquid sample is described in, for example, in WO 2007/051861, which is incorporated by reference in its entirety. Conduit 108 in fluid communication with the reaction chamber 110 connects the reaction chamber with the first end of channel 105. As described in WO 2007/051861, detection can take place in the channel. Thus, the channel is at least partially optically transparent. For example, channel 105 can be covered by an at least partially optically transmissible layer. The second end of channel 105 is connected to a first end of second zone 104 via conduit 108. The second zone is at least partially flexible so that the inner diameter of the second zone can be reduced to zero. For example, the second zone can be an elastic silicone tube or the like. A second end of the second zone is mounted into a cap 102 which is adapted to be applied to the substrate and to support the second zone. By opening the cap, tight connection 109 between the first and the second zone is opened, by closing the cap, the tight connection 109 between the first and the second zone is closed.

In shipping condition the device can be closed, i.e., the second zone forms a tight connection with the first zone at connection 109. Alternatively, the device can be shipped in an open state. In some embodiments, the device includes (e.g., for safety purposes) a mechanism configured to prevent the cartridge from becoming opened after it is first closed. Connection 109 is closed when a sealing member in cap 102 forms a fluid-tight connection with end of capillary 103. In operation, the user opens the cap, thereby opening the first zone on its first end. The user contacts the open end of the first zone with the sample liquid, e.g., a blood drop such as produced by a finger stick. Thus, capillary 103 fills with the sample. The user closes the cap thereby closing connection 109 between the first and the second zone. At this point, the fluid circuit includes a contiguous, predetermined volume of sample liquid, the reagent pellet, and a contiguous volume of transport fluid (e.g., air) within the reaction chamber, conduits, channel and second zone. The user puts the device into the machine designed for operating the device. The machine includes an actuator configured to compress the second zone, a detector, and a controller. The actuator compresses the second zone, reducing its diameter at the compression point to zero. When the device and the actuator are moved relative to each other while in a compressed state, the pressure in the transport fluid will increase on the one end of the sample volume while it will decrease on the other end of the sample volume. The sample volume will move within the fluid circuit until the pressure on each end of the sample volume is equal.

Channel 105 can be hydrophobic, such that the sample will not move into channel 105 without application of an external force. In some embodiments, the walls in the vicinity of reagent pellet 107 can also be hydrophobic. When using hydrophilic materials the long-term stability of the reagent pellet can be worse compared to a hydrophobic material.

In one embodiment, the actuator is fixed within the machine and the device is moved relative to the means for compressing. As described in WO 2007/051861, the actuator is e.g. a roller.

The device can be moved within the machine such that the sample will move into the reaction chamber thereby dissolving the reagent pellet in this chamber. The antibodies will bind to the respective antigens present in the sample. Depending on the type of sample, antigens may be located on particles suspended in the sample liquid (e.g., on cell surfaces in a blood sample). Because the antibodies are labelled (e.g., with a fluorescent dye), once bound to their respective antigens, the antigens become labelled as well. See, e.g., WO 2007/051861. By further moving the device relative to the machine in the same direction the sample is moved into the channel. Once the channel is filled, detection takes place.

Desirably, the detector is small, inexpensive, and versatile; that is, it is adaptable to other applications than solely the use described here. The detector can be a fluorescence microscope, preferably one that has very small outer dimensions and a small height with respect to the cartridge. The detector can be capable of imaging objects with a size ≥5 μm and is configured to detect signals of the wavelength which are emitted by the fluorescent dyes used in the assay. The light source can be a high-power LED emitting light in a spectrum which is suitable to excite the fluorescent dyes used in the assay. If different dyes are used, e.g. at least two different dyes emitting light at two different wave lengths, detection should be possible at each of at least two different wavelengths. The detector can include a focus mechanism and a camera.

Usually, very strong light sources are used for fluorescence microscopy, because to have almost parallel light beams, only a small portion of the emitted light is used (solid angle ~2°). By using a condenser lens and detector lens that collects a greater portion of light emitted from the source, a less powerful source (e.g., an LED) can be used. Fluorescence microscopy traditionally places a very high value on optical fidelity; as such, the field has taught away from high solid angles for condenser lenses. Indeed, the field has tended to teach relatively heavy, bulky, and complex optical systems for achieving high optical fidelity.

Figure 14A:
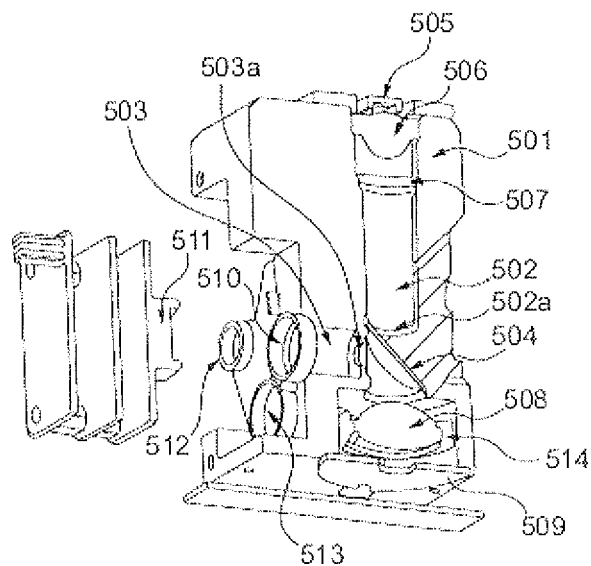
FIGS. 14A-14B show cutaway views of a fluorescence detector.
Figure 14B:
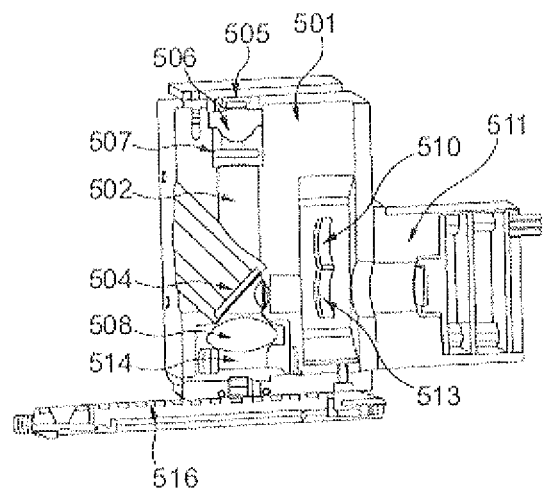

With reference to FIG. 14, an exemplary detector 500 includes a main body 501 which includes a first optical path 502 and a second optical path 503. In certain examples, each of the optical paths, independently, can have a generally cylindrical shape or other suitable configuration. First optical path 502 represents the excitation optical path; second optical 503 represents the detection optical path.

First optical path 502 connects light source 505 with cartridge 516. Light source 505 can be a high power LED (such as a Platinum Dragon® LED (Osram)) with emission wavelengths of 455 nm, 470 nm and 528 nm and a viewing angle of 120° (Lambertian emitter). When using fluorescent dyes the light source is selected according to the excitation wavelength of the fluorescent dyes which are used in the assay. E.g., when using phycoerythrine and phycoerythrine-Cy5 the light source is selected to emit light with a wavelength of around 520 nm while for the use of phycoerythrine and PerCP the light source is selected to emit light around 480 nm. Condenser lens 506 (e.g., made from topaz, refraction index 1.533) condenses the light emitted by the LED into the first optical path 502. Aperture 502a is configured to allow a maximum solid angle of 13.5° or less to illuminate dichroic mirror 504. Optical path 502 also includes a band pass filter 507 (excitation filter), allowing light with a wavelength between 505 nm and 530 nm to pass. Thus, the remaining excitation wavelength would be around 528 nm.

Optical path 503 connects the CMOS camera with the object 516 via dichroic mirror 504 and is configured at an angle (shown as 90° in FIG. 14) relative to optical path 502. Optical path 503 also includes a first emission filter 510. In some embodiments, filter 510 is mounted to a filter changer 512. Filter changer 512 may include additional emission filter(s), e.g. a filter 513. Emission filters 510 and 513 can be chosen with regard to a predetermined set of emission wavelengths, e.g., the emission wavelengths of the fluorescent dye(s) used for labelling reagents in the cartridge. For example, filters 510 and 513 may be selected to pass light with wavelengths of 590 nm and 685 nm, respectively, corresponding to the emission wavelengths of phycoerythrine and phycoerythrine-Cy5. Optical path 503 includes an aperture 503a configured to allow a maximum solid angle of 13.5° on dichroic mirror 504.

Dichroic mirror 504 is configured to separate detection optical path 503 from excitation optical path 502. In some embodiments it is a short pass dichroic mirror allowing light with a wavelength <=568 nm to pass while light with a wavelength >568 nm is reflected. Thus, dichroic mirror 504 allows the light from the excitation optical path to pass while the light from the object 516 is reflected into the detection optical path. Again, physical properties of dichroic mirror 504 are selected according to the labels (e.g., the fluorescent dyes) which are used in the assay.

In some embodiments, the detector further includes a focusing mechanism 514 allowing varying the distance of detection lens 508 and object continuously by 5 mm or less, e.g. by 1 or 2 mm.

In some embodiments, detection lens 508 is configured to have a detection optical aperture of 0.4 or less, e.g. 0.2 and a excitation optical aperture of 0.5 or less, e.g. 0.4.

The detector also may include a digital imaging device such as an 8-bit grey value CMOS camera with a resolution of e.g. 640×480 pixels. In other embodiments, the digital imaging device may have a higher resolution and/or may be a colour CMOS camera.

In some embodiments, the reproduction scale of the detection system is between 1:1 and 1:10, e.g. 1:3, 1:4 or 1:5.

In some embodiments, the distance between the object 516 and the detection lens 508 is between 2 mm and 20 mm, e.g. 8 mm, 9 mm or 10 mm.

Figure 15:
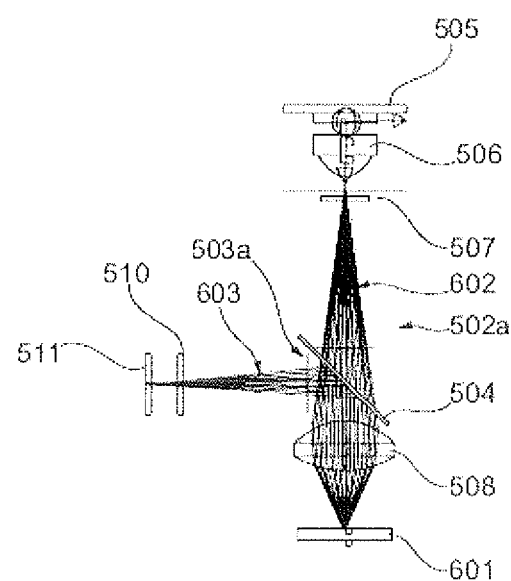
FIG. 15 shows a scheme of optical path of a detector.

With reference to FIG. 15, in operation the light emitted from the light source 505 is condensed via lens 506 and filtered via excitation filter 507. It passes aperture 502a, dichroic mirror 504, detection lens 508, aperture 509 and excites the object 601. In some embodiments, the object 516 is the channel filled with the sample liquid, e.g. blood, the liquid including a number of particles, e.g. T-helper cells to be detected. The particles may be labelled with one or more fluorescent dye coupled antibodies. In other embodiments, the object is a channel including target molecules labelled with one or more fluorescent dyes and bound to probe molecules or an array of probe molecules immobilized on one of the channel's surfaces. The dyes fluoresce under the influence of the excitation light from the LED. The light emitted from the fluorescent dyes passes aperture 509, detection lens 508 and is reflected via dichroic mirror 504 into the detection optical path 503. There it passes detection filter 510 (or 513, depending of the position of filter changer 512) adapted to allow the passage of light of a wavelength of the light emitted from the fluorescent dye. After the light has passed the filter, it is collected by the CMOS chip of the attached CMOS camera 511.

Figure 16A:
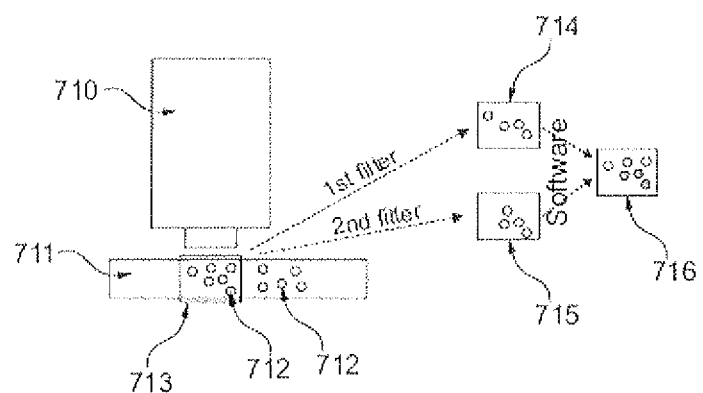
FIGS. 16A-16B show depictions of a cell counting assay using a fluorescence detector.
Figure 16B:
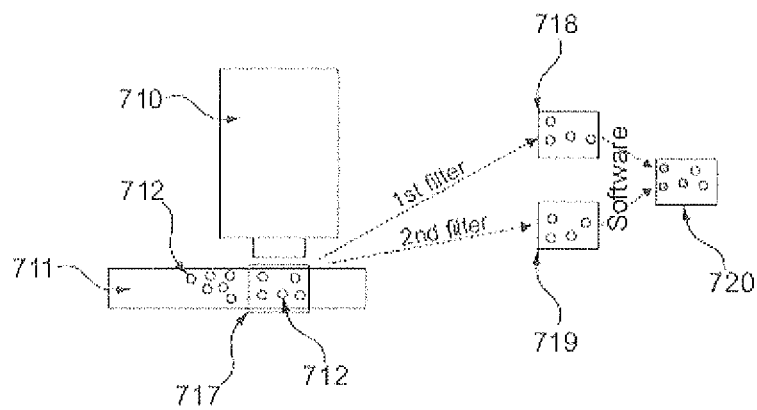

FIGS. 16A-16B illustrates how the detector can be used for detecting, e.g. the number of T-helper cells present in a blood sample. Details for the device and the reaction can be found above and in WO 2007/051861 which is incorporated herein by reference. In the example discussed, the cartridge is prepared with two labelled antibodies: phycoerythrine-labelled anti CD4 antibodies and phycoerythrine-Cy5-labelled anti-CD3 antibodies. Since T-helper cells show both antigens on their surface, T-helper cells will be labelled with both fluorescent dyes. Other cells, showing only one of the both antigens on their surfaces, may be also present in the sample. These cells will be labelled only with one of the corresponding fluorescent dyes.

After reaction with the respective fluorescent dye labelled antibodies, the liquid sample comprising fluorescing cells 712 is moved into the detection channel 711. At a first position (FIG. 16A) the detector 710 detects a first image 714 representing a view on a portion 713 of channel 711. Portion 713 represents a predetermined volume of the sample, e.g. 100 nL. Image 714 is taken with a first filter which is configured to allow light emitted by phycoerythrine-labelled anti CD4+ antibodies present in the sample and to block light emitted by phycoerythrine-Cy5-anti-CD3+ antibodies. A second image 715 of the same position is taken using a second filter which is configured to allow phycoerythrine-Cy5-anti-CD3+ antibodies and to block light emitted by phycoerythrine-labelled anti CD4+. Images 714 and 715 may show a different number of signals within portion 713. Additionally, due to aberrations in the optical system, both images 714 and 715 might be out of alignment relative to each other.

Software (e.g. Iconoclust by Clondiag) can be used to align both images 714 and 715, e.g. by using alignment marks in the channel (not shown) or by analyzing the relationships between signals which are present in both of the pictures. Additionally, the software identifies and marks the signals which have been detected in both pictures (716). In FIG. 16A, three signals were identified to be present in both figures. That means that 3 cells with both antigens were found in portion 713. The results may be displayed, used for further calculations or statistics or may be stored for further processing.

Detector 710 and channel 711 are moved relative to each other to view another portion 717 of channel 711 (FIG. 16B) and the detection procedure is repeated. Images 718 and 719 are recorded, using the first and second filters respectively. The software identifies and marks the signals which have been detected in both pictures (720).

Detection may be repeated in the additional portions of the detection channel, resulting in a set of values representing the number of cells in each of the portions. The number of cells present in the sample, as well as corresponding statistical parameters may be calculated from this set of values. For example, an average of three cells per 100 nL corresponds to a total amount of 150 cells in a sample volume of 5 µL.

Figure 17:
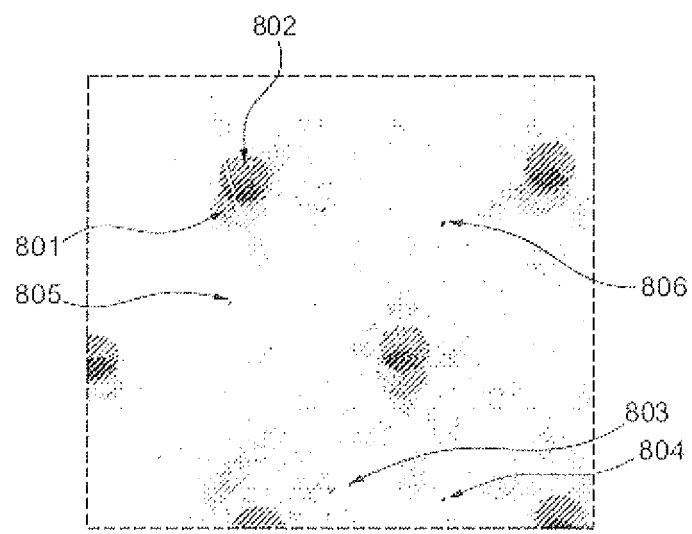
FIG. 17 shows an overlay of two images derived from a cell counting assay using a fluorescence detector.

FIG. 17 shows an overlay of two images detected during a T-cell counting experiment using blood as liquid sample. Both images are detected at the same location of the channel (e.g. like images 714 and 715 in FIG. 5) using two different detection filters. 801 and 802 represent one alignment mark imaged using two different detection filters. The dislocation between both images can clearly be detected and corrected by using the marks. 803 and 804 represent a single cell which is dislocated by the same distance like the alignment marks 801 and 802. Since this cell is present in both of the images, it can be determined that this cell is labelled with both antibodies and thus is a T-helper-cell. 805 represents a cell which is only detectable in one of the both images of the overlay. Thus it can be derived that this cell does not show both antigens on its surface and therefore is not a T-helper-cell. Other blood cells can also be seen in the images. Since they are not labelled with any fluorescent antibodies, they only can be seen as a shadow (806).

Figure 18:
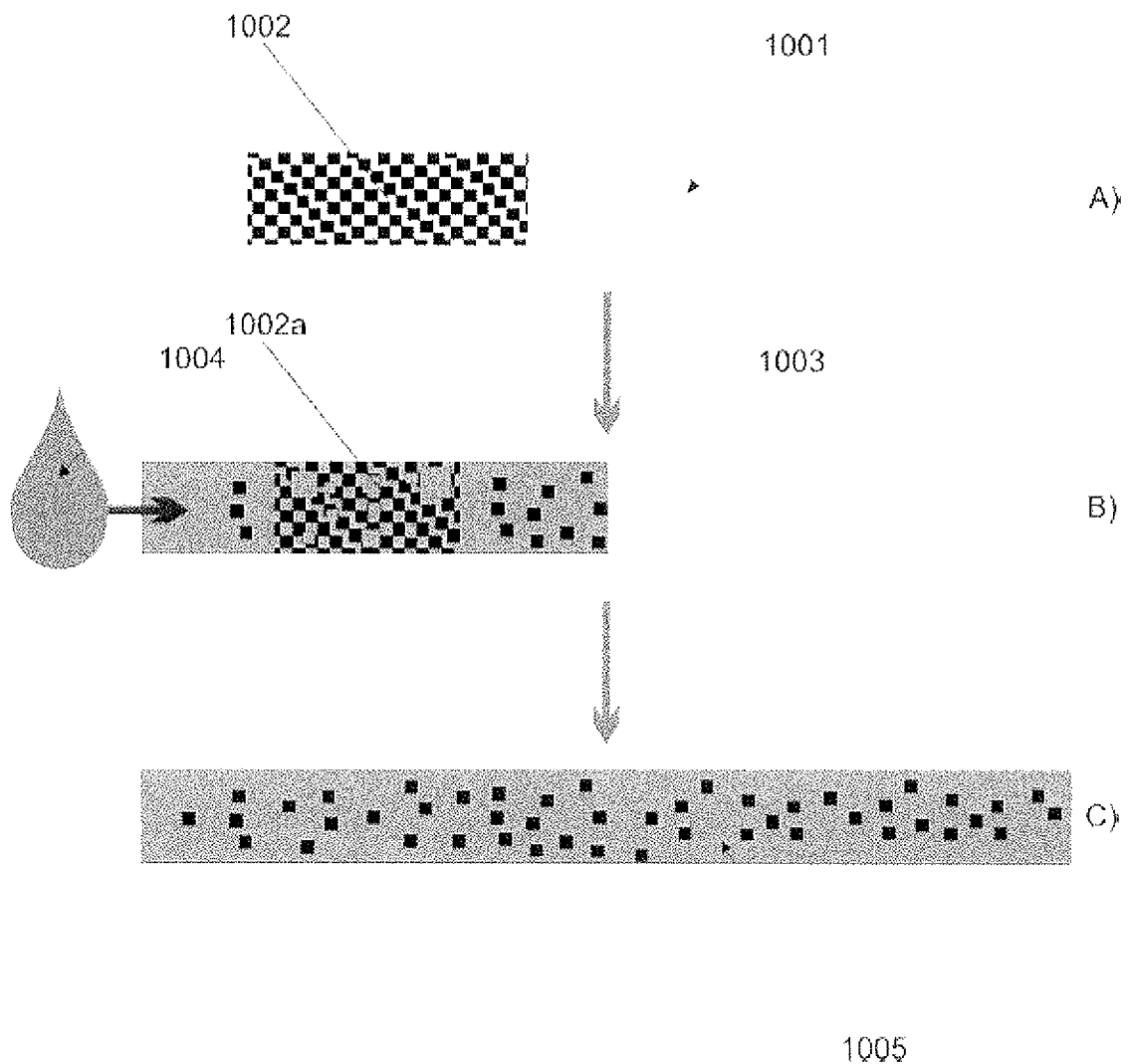
FIGS. 18A-18C illustrate a matrix included in a capillary (A) and the step of at least partially dissolving the matrix after contacting the matrix with a drop of liquid (B and C).

FIG. 18 shows a capillary 1001 including a matrix or substance cake 1002, e.g. a lyophilisate. The matrix 1002 includes various substances such as coagulation inhibitors, stabilizing reagents and labeled antibodies etc. In some embodiments, the matrix fills the complete diameter of the cartridge. In some embodiments, the matrix fills only a part of the length of the capillary. In some embodiments, the structure of the matrix allows a liquid to soak into the pellet- or cake-like matrix.

As can be seen in FIG. 18 B, when a sample 1004 is applied to the capillary it will move into it driven by capillary forces. When the sample 1004 flows through the matrix, the matrix may be dissolved (1002a) and the reagents 1003 are diluted within the sample. Dissolving the matrix is supported by the moving sample itself; the sample is soaked through the matrix into the capillary by capillary forces thereby creating a fluid flow acting on the matrix. Thus, dissolving the pellet is not only controlled by diffusion. Finally, when the capillary is filled with the sample (see FIG. 18C), the matrix may already be more or less completely dissolved. Small remains of the pellet may be dissolved now by diffusion controlled processes.

Figure 19:
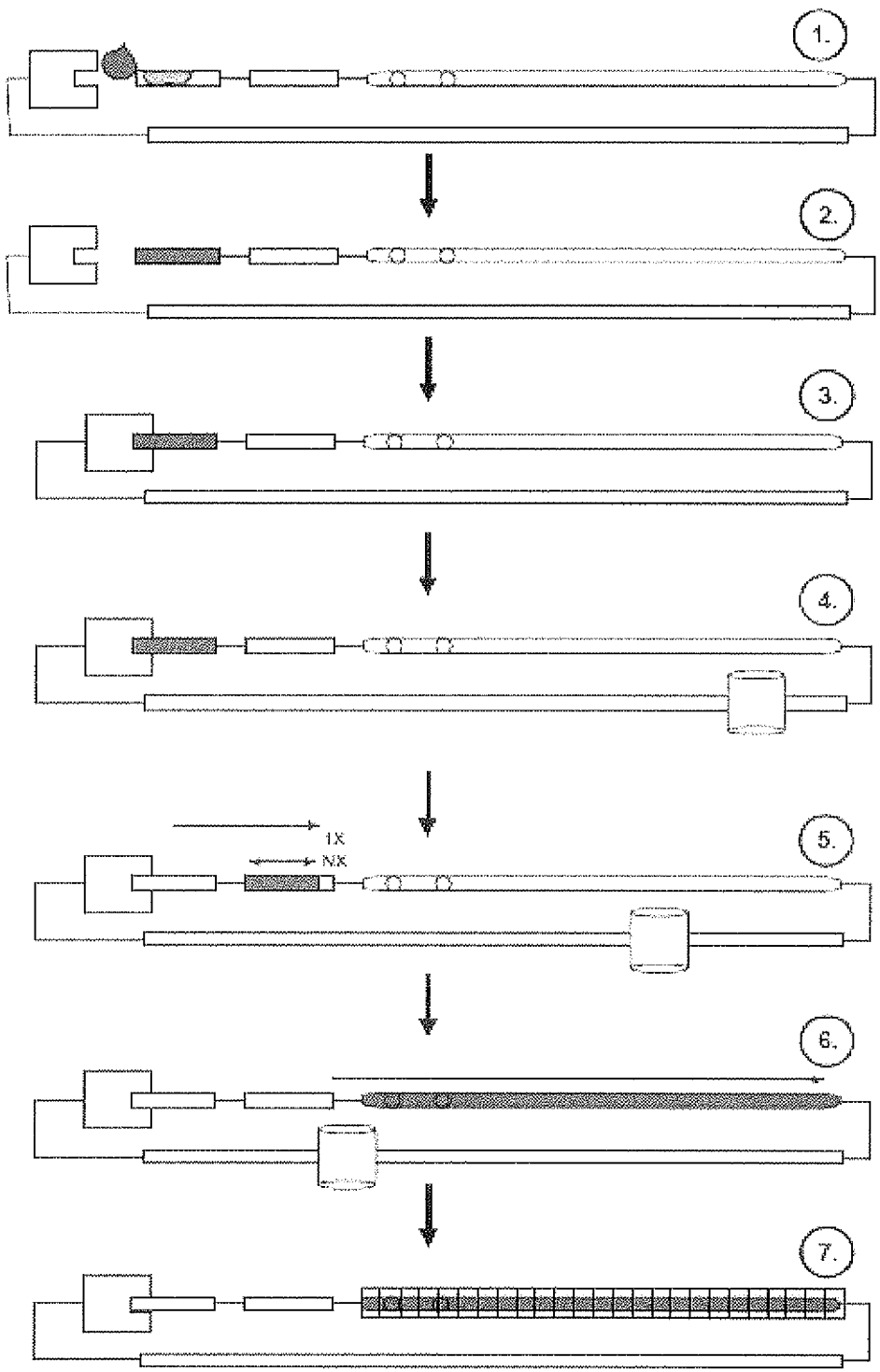
FIG. 19 illustrates the filling of a cell counting device (steps 1 to 7). Exemplary control elements comprised in the microfluidic channel are depicted as open circles.

FIG. 19 shows an exemplary embodiment for workflow in a device or cartridge. The cartridge may contain a sample port with an end-to-end capillary (to contain, e.g. 5 µl of sample) that contains dried reagents as described herein needed to perform the test. The sample is first applied to the capillary end of the cartridge (1). The sample is drawn into the end-to-end capillary by capillary force (2). The reagents provided in the capillary are re-suspended in the sample. The cartridge may have a snap-tight attached cap. After applying the sample, the cap is closed, and the cartridge is placed into the system (3). This may eliminate carryover. Complete filling of end-to-end capillary can be assessed visually, through a small window on the cartridge. The user can thus assess if sufficient sample has been taken up by the capillary before the test process has been initialized on the system. After loading the test cartridge onto the system filling is checked by the system by means of a reflectance measurement window. A roller that is part of the device or system is brought into contact with the cartridge tubing or microfluidic channel (4). The cartridge is moved along the roller. The microfluidic channel is part of a closed fluid circle or flow path. Thus, the cartridge and the roller may make up a peristaltic pump that is used to actively move the sample within the cartridge (5). The sample is first moved into a reaction containment and then repeatedly back and forth to support proper mixing of the reagent and binding of antibodies to the respective antigens. After a pre-defined incubation time the stained sample is moved into the detection containment or region and the analytes, e.g., cells, are allowed to settle for defined period of time (6). The detection channel is scanned along a fluorescence optics module and images are collected at two different wavelengths all along the channel (7).

In some embodiments, a device or system as described above may comprise a ventilation opening or opening configured to vent the microfluidic channel. Such a ventilation opening may be located between the detection region and a second end of the inlet region, e.g. a capillary inlet, which is adapted for receiving the sample. In such an embodiment, the second end is the end opposite to a first end adapted for receiving the sample. The opening may provide a fluid connection of the second end of the capillary inlet with the ambient air. Further, the capillary inlet adapted for receiving the sample may be arranged in such a manner that a movement of the capillary inlet within the microfluidic channel will allow closing the ventilation opening. The opening may be, for instance, a hole reaching through a wall of the microfluidic channel and connecting the inner end of the capillary adapted for receiving the sample with the ambient air.

Figure 20:
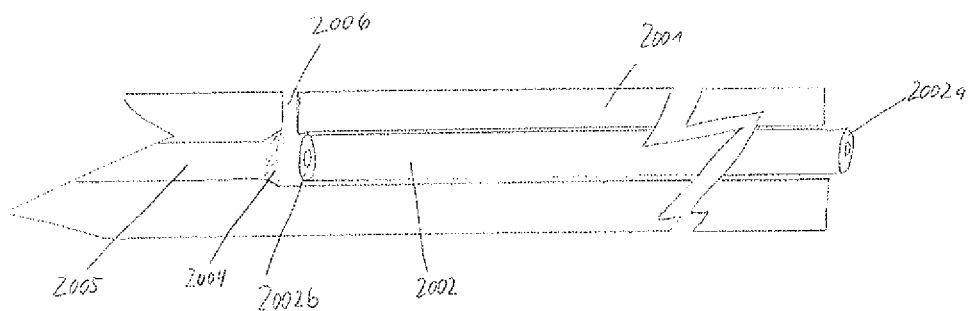
FIGS. 20 and 21 show exemplary embodiments of a device having a microfluidic channel with a ventilation opening in an open (FIG. 20) and a closed (FIG. 21) state.
Figure 21:
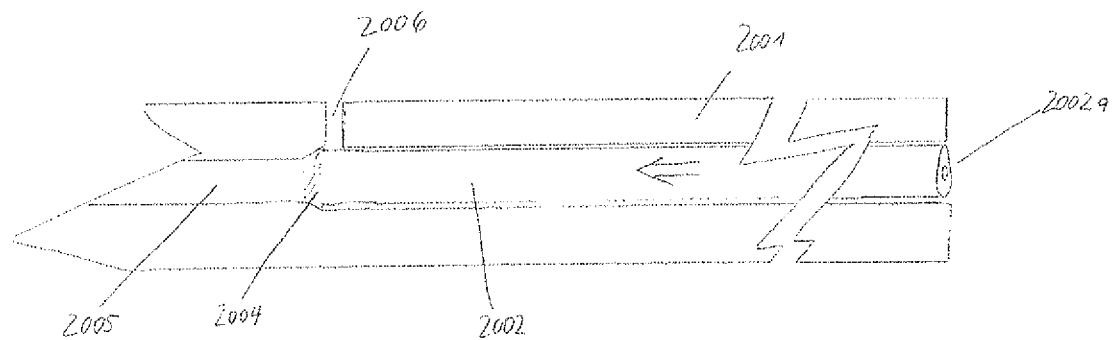

FIGS. 20 and 21 show exemplary embodiments of the ventilation opening in an open (FIG. 20) and a closed (FIG. 21) state. Here, capillary inlet 2002 is mounted into cartridge 2001 such, that the first end 2002a of capillary inlet can be brought in contact with a sample (not shown) and the second end 2002b is in fluid communication with the ambient air surrounding the cartridge 2001 via opening 2006 and with channel 2005 via structure 2004. Structure 2004 may be adapted to form a tight connection between the second end 2002b of capillary inlet 2002 and channel 2005, which may lead to other compartments of the cartridge such as the detection region. After loading the sample into the capillary inlet, the capillary inlet 2002 may be moved until it contacts structure 2004 (see FIG. 22). By this movement, opening 2006 is closed and the sample can flow into channel 2005.

Figure 22:
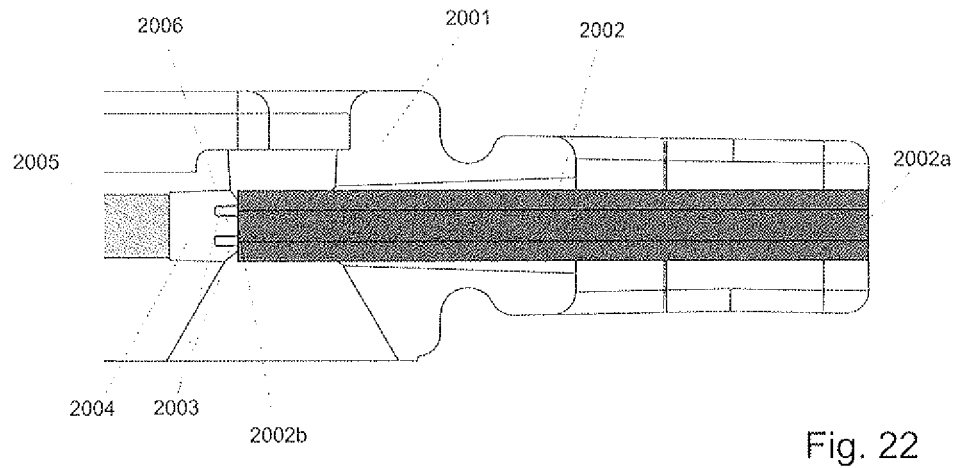
FIGS. 22 to 24 show further exemplary embodiments of a device having a microfluidic channel with a ventilation opening.
Figure 23:
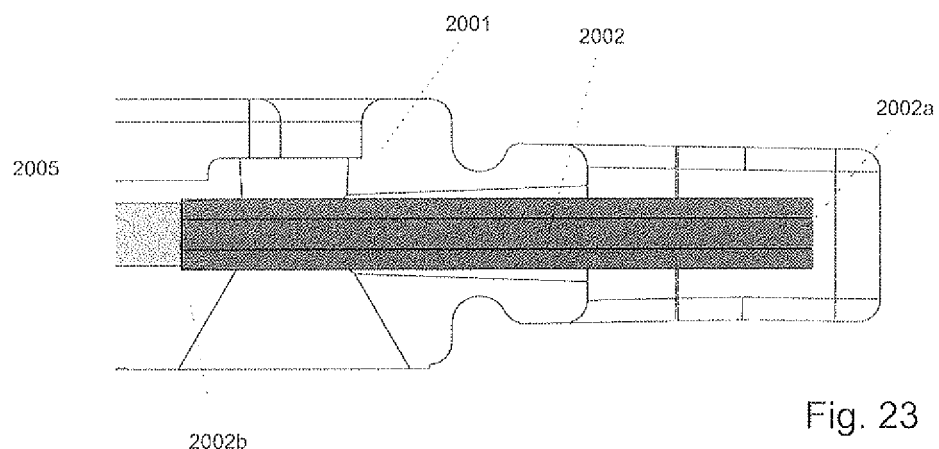
Figure 24:
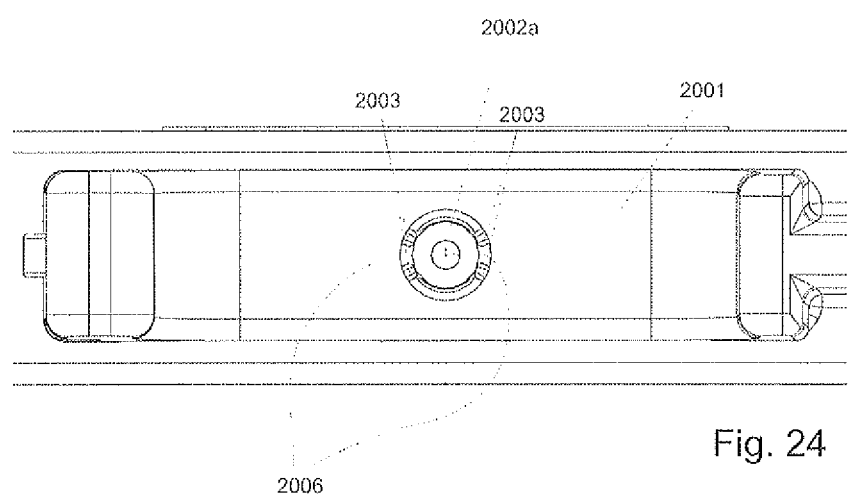

FIGS. 22-24 show detailed views of an exemplary capillary inlet adapted for receiving the sample of a device as described above. In this embodiment, the cartridge 2001 may comprise one or more, e.g. three means 2003 for supporting the capillary inlet 2002. Such means may be mounted into or may be part of cartridge 2001. The means 2003 for supporting the capillary inlet 2002 allow a positioning of the capillary inlet within the substrate as well as a movement of the capillary inlet within the substrate. The means 2003 for supporting the capillary inlet may guide the capillary inlet over the whole area where the capillary inlet is mounted into the substrate or support the capillary inlet only punctually.

As illustrated in FIG. 22, in a first state, the capillary inlet 2002 for receiving the sample is in a first position and supported by means 2003 for supporting the capillary inlet within substrate 2001. For instance, means 2003 for supporting the capillary inlet are bars which allow positioning and movement of the capillary inlet 2002 within substrate 2001. Bars 2003 may be separated from each other by gaps or openings 2006 which extend along the bars and connect structure 2004 with the ambient air. Structure 2004 allows forming a close connection with the second end 2002b of the capillary inlet 2002 and channel 2005 leading to the detection region of the microfluidic channel.

In some embodiments, structure 2004 may be a hole having an inner diameter, wherein the inner diameter is substantially equal to the outer diameter of the capillary inlet.

In other embodiments, structure 2004 may be a conical hole having a first and a second diameter. The first diameter may be adapted to form a hopper for the second end of the capillary inlet and may be substantially equal or bigger than the outer diameter of the capillary inlet; the second diameter may be adapted to form a close connection with channel 2005 and may be equal or smaller than the outer diameter of the capillary inlet.

In the first position, capillary inlet 2002 is not in contact with structure 2004. Therefore, air may be displaced directly from the capillary inlet to the ambient air via the gaps or openings 2006 between the bars 2003, for instance by filling the capillary inlet with the sample.

In FIG. 23, capillary inlet 2002 for receiving the sample is in a second position. In this embodiment, a close connection between the capillary inlet 2002 and channel 2005 is formed via structure 2004. The connection can be closed, for instance, by moving the capillary inlet 2002 on bars 2003 toward channel 2005. The movement can be initiated or caused by applying an external force on the first end 2002a of capillary inlet 2002. The external force can be applied, for instance, manually, automatically in a device operating the cartridge or when closing a cap of the cartridge.

FIG. 24 shows a top view on the first end 2002a of capillary inlet 2002. In addition, means 2003 for supporting the capillary inlet 2002 and gaps or openings 2006 are shown.

The following additional embodiments are also provided:

Item 1 A device for detecting an analyte, comprising a cartridge having a microfluidic channel including an inlet and a detection region in fluid communication with the inlet a microfluidic flow path having an at least partially deformable wall and in fluid communication with the detection region of the channel; and a cap having: a sealing member configured to seal with the inlet and form a fluid circuit including the inlet, the microfluidic channel and the microfluidic flow path.

Item 2 The device of item 1, wherein the cap and cartridge are configured to close irreversibly after forming the fluid circuit.

Item 3 The device of item 1, wherein the cap is flexibly attached to the cartridge.

Item 4 The device of item 1, wherein the cap and cartridge are configured to engage in a first relative position such that the cap can be removed and to engage in a second relative position such that the cap is irreversibly closed after forming the fluid circuit.

Item 5 The device of item 1, wherein the detection region is bounded by at least one surface of the cartridge and at least one surface of a lid.

Item 6 The device of item 5, wherein the lid includes a transparent film over the detection region.

Item 7 The device of item 6, wherein the lid is adhesively affixed to the cartridge.

Item 8 A system for detecting an analyte, comprising a cartridge having a microfluidic channel including an inlet and a detection region in fluid communication with the inlet; a microfluidic flow path having an at least partially deformable wall and in fluid communication with the detection region of the channel; and a cap having: a sealing member configured to seal with the inlet and form a fluid circuit including the inlet, the microfluidic channel and the microfluidic flow path; and a fluorescence detector including: a light source; a condenser lens obtaining a solid angle of 10° or greater; and an objective lens obtaining a solid angle of 10° or greater.

Item 9 The system of item 8, wherein the fluorescence detector includes a camera.

Item 10 The system of item 8, wherein the fluorescence detector includes one or more selectable emission filters.

Item 11 A method of detecting an analyte comprising introducing a liquid sample into a microfluidic channel thereby forming a contiguous liquid slug enclosed by the channel and bounded at a first end by a transport fluid; forming a fluid circuit such that the transport fluid provides fluid communication between the first and second ends of the liquid slug; and applying a differential pressure to the first and second ends of the liquid slug via the transport fluid.

Item 12 The method of item 11, wherein a portion of the fluid circuit is formed by an elastically deformable wall.

Item 13 The method of item 12, wherein applying a differential pressure to the first and second ends of the liquid slug includes compressing the elastically deformable wall.

Item 14 The method of item 11, further comprising labeling the analyte with a first fluorescent antibody and a second fluorescent antibody, wherein the first and second fluorescent antibodies have distinct emission wavelengths.

Item 15 The method of item 14, wherein detecting the analyte includes recording a first image of the analyte at the emission wavelength of the first fluorescent antibody; recording a second image of the analyte at the emission wavelength of the second fluorescent antibody; and comparing the first and second images.

Item 16 A method, comprising introducing a liquid sample into a microfluidic channel thereby forming a contiguous liquid slug enclosed by the channel and bounded at a first end by a transport fluid, the liquid sample comprising multiple particles, forming a fluid circuit such that the transport fluid provides fluid communication between the first and second ends of the liquid slug, forming a mixture comprising at least a portion of the liquid sample and an optical label by applying a differential pressure to the first and second ends of the liquid slug via the transport fluid, forming multiple complexes, each complex comprising one of the multiple particles and at least one of the optical labels, and detecting complexes present within a subset of the mixture.

Item 17 The method of item 16, wherein a portion of the fluid circuit is formed by an elastically deformable wall.

Item 18 The method of item 17, wherein applying a differential pressure to the first and second ends of the liquid slug includes compressing the elastically deformable wall.

Item 19 The method of any of items 16 to 18, further comprising detecting complexes present within each of multiple different subsets of the mixture.

Item 20 The method of item 19, wherein a total volume of the multiple different subsets is at least 90% of a volume of the liquid sample introduced to the microfluidic device.

Item 21 The method of any of items 16 to 20, comprising introducing a total volume V of liquid sample to the microfluidic device and wherein a total volume of the mixture is at least 90% of the volume V.

Item 22 The method of item 21, wherein the mixture comprises at least about 95% of the volume V of liquid sample.

Item 23 The method of item 20, comprising detecting complexes present within at least 10% of the total volume of the mixture.

Item 24 The method of any of items 16 to 23, wherein the particles are cells and the optical labels are fluorescent labels.

Item 25 The method of any of items 16 to 23, wherein the microfluidic channel includes an inlet and a detection region in fluid communication with the inlet and is a microfluidic channel of a microfluidic device.

Item 26 The method of any of items 11 to 25, further comprising, prior to introducing a liquid sample into a microfluidic channel, introducing a liquid sample to a bore of a capillary.

Item 27 The method of item 26, further comprising, intermediate the steps of introducing the liquid sample to the bore of the capillary and introducing the liquid sample into the microfluidic channel, connecting the capillary to the microfluidic device, the liquid sample remaining within the capillary.

Item 28 The method of any of items 11 to 27, further comprising optically detecting a signal indicative of an amount of complex present within a subset of the liquid sample, the subset being present within a detection region of the microfluidic device.

Item 29 The method of any of items 11 to 28, wherein introducing the liquid sample into the microfluidic channel is performed by compressing the elastically deformable wall.

Item 30 The method of item 29, wherein compressing the elastically deformable wall comprises compressing a first portion of the fluid circuit and, without first completely releasing the compression, moving a site of the compression along the fluid circuit by an amount sufficient to perform the step of introducing.

Item 31 The method of any of items 11 to 30, comprising performing the step of optically detecting a signal indicative of an amount of complex present within the subset with first completely releasing the compression.

Item 32 The method of any of items 11 to 31, where the liquid sample is blood.

Item 33 The method of any of items 26 to 32, wherein the capillary bore comprises a coagulation inhibitor.

Item 34 The method of any of items 26 to 33, comprising intermediate the steps of introducing the liquid sample to the bore of the capillary and introducing at least the portion of the liquid sample into the microfluidic channel, stopping the liquid sample from exiting the capillary.

Item 35 The method of any of items 11 to 34, wherein a detection region of the microfluidic channel does not support capillary flow of the liquid sample.

Item 36 The method of any of items 11 to 35, wherein at least a part of an interior surface of the microfluidic channel is hydrophobic.

Item 37 The method of any of items 26 to 36, further comprising moving at least one of the microfluidic device and an optical detector with respect to one another and subsequently detecting an optical signal indicative of an amount of complex present within a different subset of the liquid sample.

Item 38 The method of any of items 26 to 37, wherein the capillary is an end to end capillary comprising first and second open ends, the bore of the capillary comprises a total volume V, and the step of introducing at least a portion of the liquid sample comprises introducing at least 90% of the liquid sample into the microfluidic channel.

Item 39 A device configured to perform any of the method of items 11 to 38.

Item 40 A device for detecting an analyte, comprising a cartridge having a microfluidic channel including a capillary inlet having an anticoagulant on an inner surface, a chamber including a reagent, and a detection region in fluid communication with the inlet; a microfluidic flow path having an at least partially deformable wall and in fluid communication with the detection region of the channel; and a cap having a sealing member configured to seal with the inlet and form a fluid circuit including the inlet, the microfluidic channel and the microfluidic flow path.

Item 41 A fluorescence detector including a light source; a condenser lens obtaining a solid angle of 10° or greater; and an objective lens obtaining a solid angle of 10° or greater and being configured to image a microscopic object.

Item 42 A method, comprising introducing a liquid sample to a bore of a capillary, and introducing at least a portion of the liquid sample into a microfluidic network of the microfluidic device by reducing a pressure acting on a liquid sample-gas interface of the liquid sample.

Item 43 The method of item 42, further comprising, subsequent to the step of introducing the liquid sample to the bore of the capillary, connecting the capillary to a microfluidic device, the liquid sample remaining within the capillary.

Item 44 The method of item 42 or 43, wherein the reducing a pressure is performed by compressing at least a portion of the microfluidic network to displace gas therefrom and subsequently decompressing the at least a portion of the microfluidic network.

Item 45 The method of any of items 42 to 44, wherein the microfluidic network is at least in part defined by and between first and second generally planar substrates, at least one of the substrates being deformable upon the application of external pressure to compress the at least a portion of the microfluidic network and the at least one substrate tending to resume its previous position upon release of the external pressure to permit decompression of the at least a portion of the microfluidic network.

Item 46 The method of any of items 42 to 44, wherein the microfluidic network is at least in part defined by a microfluidic channel including an inlet and a detection region in fluid communication with the inlet, and a microfluidic flow path in fluid communication with the detection region, wherein the microfluidic flow path has a wall being at least partially deformable upon the application of external pressure to compress the at least a portion of the microfluidic flow path, and the wall tends to resume its previous position upon release of the external pressure to permit decompression of the at least a portion of the microfluidic flow path.

Item 47 The method of any of items 42 to 46, further comprising combining the liquid sample with the one or more reagents present within the microfluidic network to form a mixture.

Item 48 The method of item 47, wherein the mixture comprises at least 90% of the liquid sample that was introduced to the microfluidic network.

Item 49 The method of item 47 or 48, wherein the one or more reagents include a detectable label that react with the sample to form a complex including the label and an analyte present in the sample.

Item 50 The method of any of items 47 to 49, further comprising optically detecting a signal indicative of an amount of complex present within a subset of the liquid sample, the subset being present within a detection zone of the microfluidic device.

Item 51 The method of item 50, further comprising displacing the subset of liquid sample from the detection zone and introducing a different subset of the liquid sample into the detection zone and optically detecting a signal indicative of an amount of complex present within the different subset.

Item 52 The method of item 51, wherein displacing the subset and introducing the different subset is performed by compressing at least a portion of the microfluidic network, the compressed portion being at least partially offset along the network from the detection zone.

Item 53 The method of item 52, wherein compressing the at least a portion comprises compressing a first portion of the microfluidic network and, without first completely releasing the compression, moving a site of the compression along the microfluidic network by an amount sufficient to perform the steps of displacing and introducing.

Item 54 The method of item 53, comprising performing the step of optically detecting a signal indicative of an amount of complex present within the different subset without first completely releasing the compression of the microfluidic network.

Item 55 The method of any of items 42 to 54, where the liquid sample is blood.

Item 56 The method of item 55, wherein the capillary bore comprises a coagulation inhibitor.

Item 57 The method of any of items 42 to 56, comprising intermediate the steps of introducing the liquid sample to the bore of the capillary and introducing at least the portion of the liquid sample into the microfluidic network, stopping the liquid sample from exiting the capillary.

Item 58 The method of item 57, wherein stopping the liquid sample from exiting the capillary comprises increasing the pressure acting on the liquid sample-gas interface.

Item 59 The method of any of items 42 to 58, wherein the microfluidic network does not support capillary flow of the liquid sample.

Item 60 The method of item 59, wherein an interior surface of the microfluidic network that is defined by at least one of the first and second substrates is hydrophobic.

Item 61 The method of any of items 42 to 60, wherein the analyte is a particle.

Item 62 The method of item 61, wherein the particle is a cell.

Item 63 The method of item 49, further comprising moving at least one of the microfluidic device and an optical detector with respect to one another and subsequently detecting an optical signal indicative of an amount of complex present within a different subset of the liquid sample.

Item 64 The method of any of items 42 to 63, wherein the capillary is an end to end capillary comprising first and second open ends, the bore of the capillary comprises a total volume V, and the step of introducing at least a portion of the liquid sample comprises introducing at least 90% of the liquid sample into the microfluidic network.

Item 65 A device configured to perform any of items 42 to 64.

Item 66 A method, comprising introducing a liquid sample to a microfluidic network disposed between an inner surface of a first substrate and an inner surface of a second substrate of a microfluidic device, at least one of the substrates being flexible, the liquid sample comprising multiple particles, forming a mixture comprising at least a portion of the liquid sample and an optical label by sequentially reducing a distance between the inner surfaces of the first and second substrates at multiple positions within the microfluidic network, forming multiple complexes, each complex comprising one of the multiple particles and at least one of the optical labels, and detecting complexes present within a subset of the mixture.

Item 67 The method of item 66, further comprising detecting complexes present within each of multiple different subsets of the mixture.

Item 68 The method of items 66 or 67, wherein a total volume of the multiple different subsets is at least 90% of a volume of the liquid sample introduced to the microfluidic device.

Item 69 The method of any of items 66 to 68, comprising introducing a total volume V of liquid sample to the microfluidic device and wherein a total volume of the mixture is at least 90% of the volume V.

Item 70 The method of item 68, comprising detecting complexes present within at least 90% of the total volume of the mixture.

Item 71 The method of any of items 66 to 70, wherein the particles are cells and the optical labels are fluorescent labels.

Item 72 A method, comprising introducing a total volume V of a liquid sample to a microfluidic network disposed between an inner surface of a first substrate and an inner surface of a second substrate of a microfluidic device, at least one of the substrates being flexible, the liquid sample comprising multiple particles, forming a mixture within the microfluidic network, the mixture comprising at least about 90% of the volume V of liquid sample and an optical label, forming multiple complexes, each complex comprising one of the multiple particles and at least one of the optical labels, and detecting complexes present within a subset of the mixture.

Item 73 The method of item 72, wherein the mixture comprises at least about 95% of the volume V of liquid sample.

Item 74 The method of item 72 or 73, further comprising detecting complexes present within each of multiple different subsets of the mixture.

Item 75 The method of item 74, wherein a total volume of the multiple different subsets is at least 90% of a volume of the liquid sample introduced to the microfluidic device.

Item 76 A device configured to perform any of the method of items 66 to 75.

Other embodiments are within the scope of the claims.

The invention claimed is:

1. A device for detecting an analyte in a sample, comprising:
   a cartridge having:
      a microfluidic channel including a capillary inlet having a matrix;
      and a detection region in fluid communication with the capillary inlet;
      a microfluidic flow path in a closed fluid circuit having an at least partially deformable wall and in fluid communication with the detection region of the channel.

2. The device of claim 1, wherein said matrix comprises a detectable label that reacts with the analyte to from a complex including the label and/or a coagulation inhibitor and/or a stabilizing agent.

3. The device of claim 2, wherein said matrix is at least partially dissolvable in the sample.

4. The device of claim 3, wherein said matrix comprises freeze-dried components.

5. The device of claim 1, wherein the microfluidic channel comprises a first end and a second end and between the first and the second end the capillary inlet, the detection region, and an opening configured to vent the microfluidic channel.

6. The device of claim 5, wherein the opening is configured to remove gas from the microfluidic channel.

7. The device of claim 6, wherein the opening is located between the inlet region and the detection region.

8. The device of claim 7, wherein the opening is configured to remove gas from the inlet region during filling of the device with the sample.

9. The device of claim 8, wherein the opening is closable.

10. The device of claim 9, wherein the inlet region is movable within the microfluidic channel.

11. The device of claim 10, wherein the inlet region is movable with respect to the opening.

12. The device of claim 11, wherein the inlet region is movable along a longitudinal axis of the microfluidic channel.

13. The device of any of claim 12, wherein the opening, in a first relative position of the inlet region within the microfluidic channel, is in fluid communication with the inlet region, and, in a second relative position of the inlet region within the microfluidic channel, is closed.

14. The device of claim 13, wherein said device further comprises a cap having a sealing member configured to seal with the inlet region, wherein the cap is arranged such that closing of the cap moves the inlet region from the first relative position within the microfluidic channel to the second relative position within the microfluidic channel to form a closed fluid circuit including the inlet region, the detection region and the microfluidic flow path.

15. The device of claim 4, wherein the microfluidic channel comprises a first end and a second end and between the first and the second end the capillary inlet, the detection region, and an opening configured to vent the microfluidic channel.

* * * * *